(12) United States Patent
Reams et al.

(10) Patent No.: US 10,590,350 B2
(45) Date of Patent: *Mar. 17, 2020

(54) APPARATUSES AND METHODS FOR ENERGY EFFICIENT SEPARATIONS INCLUDING REFINING OF FUEL PRODUCTS

(71) Applicants: THE REGENTS OF THE UNIVERSITY OF MICHIGAN, Ann Arbor, MI (US); GOVERNMENT OF THE UNITED STATES as represented by THE SECRETARY OF THE AIR FORCE, Wright-Patterson Air Force Base, OH (US)

(72) Inventors: Josiah T. Reams, Lancaster, CA (US); Andrew Guenthner, Lancaster, CA (US); Joseph Mabry, Lancaster, CA (US); Kevin Lamison, Lancaster, CA (US); Anish Tuteja, Ann Arbor, MI (US); Arun K. Kota, Fort Collins, CO (US); Gibum Kwon, Ann Arbor, MI (US)

(73) Assignees: THE REGENTS OF THE UNIVERSITY OF MICHIGAN, Ann Arbor, MI (US); The Government of the United States, as represented by the Secretary of the Air Force, Wright-Patterson Air Force Base, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/870,524

(22) Filed: Jan. 12, 2018

(65) Prior Publication Data

US 2018/0134970 A1 May 17, 2018

Related U.S. Application Data

(63) Continuation of application No. 15/027,983, filed as application No. PCT/US2014/059727 on Oct. 8, 2014, now Pat. No. 9,868,911.

(Continued)

(51) Int. Cl.
*C10G 31/09* (2006.01)
*C10G 33/06* (2006.01)
(Continued)

(52) U.S. Cl.
CPC .......... *C10G 31/09* (2013.01); *B01D 11/0415* (2013.01); *B01D 11/0492* (2013.01);
(Continued)

(58) Field of Classification Search
CPC ............ B01D 11/0415; B01D 11/0492; B01D 61/246; B01D 69/02; B01D 61/801;
(Continued)

(56) References Cited

U.S. PATENT DOCUMENTS 3,891,496 A  6/1975  Erwin
3,922,403 A  11/1975  Sample, Jr. et al.
(Continued)

FOREIGN PATENT DOCUMENTS

EP   2118189 A1   11/2009
EP   2449001 A1   5/2012
(Continued)

OTHER PUBLICATIONS

International Search Report and Written Opinion for PCT/US2014/060162, dated Apr. 6, 2015; ISA/KR.
(Continued)

*Primary Examiner* — Medhanit W Bahta
(74) *Attorney, Agent, or Firm* — Harness, Dickey & Pierce, P.L.C.

C10L 1/36; C10L 2200/0476; C10L 2270/026; C10L 2270/04; C10L 2290/544; C10L 2290/547; C02F 1/40; C02F 1/44; C02F 2101/32; C02F 2101/325; Y10T 428/249953; Y10T 428/249978

See application file for complete search history.

(57) ABSTRACT

In various aspects, methods and apparatuses for liquid-liquid extraction are provided. In certain aspects, an emulsion can be formed by combining a feed stream, an extractant, and a surfactant. The feed stream comprises a plurality of distinct components including a first component to be removed therefrom. The feed stream may be selected from a group consisting of: a hydrocarbon feed stream and an azeotrope. Then, a portion of the first component is extracted from the feed stream (or emulsion) by contact with a superoleophobic and hygroscopic membrane filter that facilitates passage of the first component and extractant through the superoleophobic and hygroscopic membrane filter. A purified product is collected having the portion of the first component removed. Such methods are particularly useful for refining fuels and oils and separating azeotropes and other miscible component systems. Energy-efficient, continuous single unit operation apparatuses for conducting such separation techniques are also provided.

11 Claims, 9 Drawing Sheets

Related U.S. Application Data

(60) Provisional application No. 61/888,557, filed on Oct. 9, 2013.

(51) Int. Cl.

| | | |
|---|---|---|
| *C07C 29/86* | (2006.01) | |
| *B01D 11/04* | (2006.01) | |
| *B01D 61/24* | (2006.01) | |
| *B01D 69/02* | (2006.01) | |
| *C10G 21/00* | (2006.01) | |
| *C10L 1/02* | (2006.01) | |
| *C10L 1/04* | (2006.01) | |
| *C02F 1/40* | (2006.01) | |
| *C02F 1/44* | (2006.01) | |
| *B01D 69/12* | (2006.01) | |
| *B01D 69/10* | (2006.01) | |
| *C02F 101/32* | (2006.01) | |

(52) U.S. Cl.
CPC .......... *B01D 61/246* (2013.01); *B01D 69/02* (2013.01); *C07C 29/86* (2013.01); *C10G 21/00* (2013.01); *C10G 33/06* (2013.01); *C10L 1/026* (2013.01); *C10L 1/04* (2013.01); *B01D 69/10* (2013.01); *B01D 69/12* (2013.01); *B01D 2325/36* (2013.01); *C02F 1/40* (2013.01); *C02F 1/44* (2013.01); *C02F 2101/32* (2013.01); *C02F 2101/325* (2013.01); *C10G 2300/202* (2013.01); *C10G 2400/02* (2013.01); *C10G 2400/04* (2013.01); *C10G 2400/08* (2013.01); *C10G 2400/28* (2013.01); *C10L 2200/0476* (2013.01); *C10L 2270/026* (2013.01); *C10L 2270/04* (2013.01); *C10L 2290/544* (2013.01); *C10L 2290/547* (2013.01); *Y10T 428/249953* (2015.04); *Y10T 428/249978* (2015.04)

(58) Field of Classification Search
CPC .... B01D 69/10; B01D 69/12; B01D 2325/36; C07C 29/86; C10G 21/00; C10G 31/09; C10G 33/06; C10G 2400/08; C10G 2400/28; C10G 2300/202; C10G 2400/02; C10G 2400/04; C10L 1/026; C10L 1/04;

(56) References Cited

U.S. PATENT DOCUMENTS

| | | |
|---|---|---|
| 4,026,874 A | 5/1977 | Sample, Jr. et al. |
| 4,119,485 A | 10/1978 | Erwin |
| 4,127,164 A | 11/1978 | Erwin |
| 4,201,664 A | 5/1980 | Hekal |
| 4,556,623 A | 12/1985 | Tamura et al. |
| 5,199,486 A | 4/1993 | Balmer et al. |
| 5,266,222 A | 11/1993 | Willis et al. |
| 5,269,935 A | 12/1993 | Clough et al. |
| 5,385,175 A | 1/1995 | Rivero et al. |
| 5,518,610 A | 5/1996 | Pierpoline |
| 6,096,380 A | 8/2000 | Takebe et al. |
| 6,716,919 B2 | 4/2004 | Lichtenhan et al. |
| 7,157,117 B2 | 1/2007 | Mikhael et al. |
| 7,193,015 B1 | 3/2007 | Mabry et al. |
| 7,217,683 B1 | 5/2007 | Blanski et al. |
| 7,695,629 B2 | 4/2010 | Salamitou et al. |
| 7,868,112 B2 | 1/2011 | Oikawa et al. |
| 7,897,667 B2 | 3/2011 | Mabry et al. |
| 8,177,985 B2 | 5/2012 | Akay et al. |
| 8,227,381 B2 | 7/2012 | Rodrigues et al. |
| 8,562,839 B2 | 10/2013 | Cho |
| 9,186,631 B2 | 11/2015 | Tuteja et al. |
| 9,394,408 B2 | 7/2016 | Ramirez et al. |
| 9,650,518 B2 | 5/2017 | Meuler et al. |
| 9,765,255 B2 | 9/2017 | Guenthner et al. |
| 9,834,459 B2 | 12/2017 | Tuteja et al. |
| 9,868,911 B2 | 1/2018 | Reams et al. |
| 10,202,711 B2 | 2/2019 | Tuteja et al. |
| 10,220,351 B2 | 3/2019 | Tuteja et al. |
| 2001/0044030 A1 | 11/2001 | Veerasamy et al. |
| 2002/0164443 A1 | 11/2002 | Oles et al. |
| 2004/0067339 A1 | 4/2004 | Gandon et al. |
| 2004/0068075 A1 | 4/2004 | Lichtenhan et al. |
| 2004/0209139 A1 | 10/2004 | Extrand |
| 2006/0286555 A1 | 12/2006 | Van Beuningen et al. |
| 2007/0066078 A1 | 3/2007 | Kugler et al. |
| 2007/0224391 A1 | 9/2007 | Krupenkin et al. |
| 2007/0237947 A1 | 10/2007 | Gleason et al. |
| 2008/0015298 A1 | 1/2008 | Xiong et al. |
| 2008/0146734 A1 | 6/2008 | Youngblood et al. |
| 2008/0199805 A1 | 8/2008 | Rushkin et al. |
| 2008/0221262 A1 | 9/2008 | Mabry et al. |
| 2008/0240479 A1 | 10/2008 | Linford et al. |
| 2008/0241512 A1 | 10/2008 | Boris et al. |
| 2008/0314820 A1 | 12/2008 | Prulhiere et al. |
| 2009/0011222 A1 | 1/2009 | Xiu et al. |
| 2010/0035070 A1 | 2/2010 | Moorlag et al. |
| 2010/0050871 A1 | 3/2010 | Moy et al. |
| 2010/0316842 A1 | 12/2010 | Tuteja et al. |
| 2011/0084421 A1 | 4/2011 | Soane et al. |
| 2011/0229706 A1 | 9/2011 | Epstein et al. |
| 2011/0281121 A1 | 11/2011 | He et al. |
| 2011/0283778 A1 | 11/2011 | Angelescu et al. |
| 2012/0000853 A1 | 1/2012 | Tuteja et al. |
| 2012/0160362 A1 | 6/2012 | Smith et al. |
| 2012/0223011 A1 | 9/2012 | Moon et al. |
| 2013/0072609 A1 | 3/2013 | Haddad et al. |
| 2013/0081812 A1 | 4/2013 | Green et al. |
| 2013/0122225 A1 | 5/2013 | Azimi et al. |
| 2013/0178568 A1 | 7/2013 | Meuler et al. |
| 2013/0264287 A1 | 10/2013 | Zhang et al. |
| 2014/0178641 A1 | 6/2014 | Leblanc et al. |
| 2014/0290699 A1 | 10/2014 | Bengaluru Subramanyam et al. |
| 2015/0065674 A1 | 3/2015 | Ramirez et al. |
| 2015/0109313 A1 | 4/2015 | Heggelund et al. |
| 2015/0136606 A1 | 5/2015 | Tuteja et al. |

(56) References Cited

U.S. PATENT DOCUMENTS

| | | |
|---|---|---|
| 2015/0353813 A1 | 12/2015 | Guenthner et al. |
| 2015/0368824 A1 | 12/2015 | Lim et al. |
| 2016/0129400 A1 | 5/2016 | Tuteja et al. |
| 2016/0251803 A1 | 9/2016 | Tuteja et al. |
| 2019/0031883 A1 | 1/2019 | Meuler et al. |

FOREIGN PATENT DOCUMENTS

| | | |
|---|---|---|
| KR | 1020130097487 A | 9/2013 |
| WO | WO-2005/068399 A1 | 7/2005 |
| WO | WO-2009/009185 A2 | 1/2009 |
| WO | WO-2010/028752 A1 | 3/2010 |
| WO | 2010042191 A1 | 4/2010 |
| WO | WO-2011/159699 A2 | 12/2011 |
| WO | 2012008970 A1 | 1/2012 |
| WO | 2012115986 A1 | 8/2012 |
| WO | WO-2013/173722 A2 | 11/2013 |
| WO | 2015054652 A2 | 4/2015 |

OTHER PUBLICATIONS

Extended European Search Report in European Application No. EP 14 85 1477, dated Apr. 26, 2017.
Basu, Bharathibai J. et al, "Surface studies on superhydrophobic and oleophobic polydimethylsiloxane-silica nanocomposite coating system," Applied Surface Science. vol. 261. pp. 807-814. (2012).
Matinlinna, Jukka P et al., "Characterization of novel silane coatings on titanium implant surfaces," Clinical Oral Implants Research. vol. 24. Issue 26. pp. 688-697. (2012).
Mueler, Adam J. et al., "Examination of wettability and surface energy in fluorodecyl POSS/polymer blends," Soft Matter, 2011, 7, pp. 10122-10134.
Zhou, Hua et al., "Fluoroalkyl Silane Modified Silicone Rubber/Nanoparticle Composite: A Super Durable, Robust Superhydrophobic Fabric Coating," Advanced Materials . vol. 24. Issue 18. pp. 2409-2412. (2012).
Zhou, Hua et al., "Robust, Self-Healing Superamphiphobic Fabrics Prepared by Two-Step Coating of Fluoro-Containing Polymer, Fluoroalkyl Silane, and Modified Silica Nanoparticles," Advanced Functional Materials. vol. 23. Issue 13. pp. 1664-1670. (2013).
International Search Report and Written Opinion for PCT/US2014/059727, dated May 5, 2015; ISA/KR.
Adams, Richard. Technology Commercialization Opportunity Polyhedral Oligomeric Silsesquioxanes (POSS): A New Generation of Lighter Weight, Higher Performance Polymeric Materials.pp. 1-3 (Available online Jun. 9, 2010).
Chimuka, Luke, et al., "Why liquid membrane extraction is an attractive alternative in sample preparation," Pure Appl. Chem., vol. 76, No. 4, pp. 707-722 (2004).
Ehrenberg, Rachel, "Filter unmixes oil and water: Combination of chemistry and gravity could help clean spills," Science News, vol. 182, No. 7, p. 17.
Feng, Xinjian, et al., "Design and Creation of Superwetting/Antiwetting Surfaces," Advanced Materials, vol. 18, pp. 3063-3078 (2006).
Kota, Arun K., et al., "Hygro-responsive membranes for effective oil-water separation," Nature Communications, vol. 3, No. 1025, pp. 1-8 (Aug. 28, 2012).
Kota, Arun K., et al., "Superomniphobic surfaces: Design and durability," MRS Bulletin, vol. 38, pp. 383-390 (May 2013).
Kota, Arun K., et al., "The design and applications of superomniphobic surfaces," NPG Asia Materials, vol. 6, No. e109, pp. 1-16 (2014).
Kwon, Gibum et al. On-Demand Separation of Oil-Water Mixtures. Advanced Materials. vol. 24. Issue 27. pp. 3666-3671 (2012).
Mabry, Joseph M., et al., "Fluorinated Polyhedral Oligomeric Silsesquioxanes (F-POSS)," Angewandte Chemie Int. Ed., vol. 47, pp. 4137-4140 (2008) (available online Apr. 24, 2008).
Sigma-Alrdrich Fine Chemicals. Silsesquioxanes Bridging the Gap between Polymers & Ceramics. ChemFiles. vol. 1. No. 6. pp. 1-14 (2001).

The International Search Report and Written Opinion of the International Searching Authority dated Mar. 5, 2015 for PCT International Application No. PCT/US2014/059727.
The International Search Report and Written Opinion of the International Searching Authority dated Dec. 2, 2013 for PCT International Application No. PCT/US2013/041604 (Pub. No. WO 2013/73722).
Tuteja, Anish, et al., "Designing Superoleophobic Surfaces," Science, vol. 318, pp. 1618-1622 (Dec. 7, 2007).
Non-Final Office Action regarding U.S. Appl. No. 14/732,652, dated Sep. 7, 2016.
Non-Final Office Action regarding U.S. Appl. No. 13/734,446, dated Jun. 10, 2016.
Non-Final Office Action regarding U.S. Appl. No. 12/599,465, dated Aug. 19, 2016.
Non-Final Office Action regarding U.S. Appl. No. 12/599,465, dated Sep. 11, 2012.
Final Office Action regarding U.S. Appl. No. 12/599,465, dated Jan. 16, 2013.
Non-Final Office Action regarding U.S. Appl. No. 12/599,465, dated May 15, 2014.
Final Office Action regarding U.S. Appl. No. 12/599,465, dated Oct. 16, 2014.
Non-Final Office Action regarding U.S. Appl. No. 12/599,465, dated Sep. 16, 2015.
Final Office Action regarding U.S. Appl. No. 12/599,465, dated Jan. 29, 2016.
Non-Final Office Action regarding U.S. Appl. No. 13/734,446, dated May 1, 2015.
Final Office Action regarding U.S. Appl. No. 13/734,446, dated Nov. 23, 2015.
Tuteja, Anish, et al., "Design Parameters for Superhydrophobicity and Superoleophobicity." Mrs Bulletin, vol. 33, pp. 752-758 (Aug. 2008).
Tuteja, Anish, et al., "Robust Omniphobic Surfaces." PNAS, vol. 105. No. 14, pp. 18200-18205 (Nov. 25, 2008).
Choi, Wonjae, et al., "Fabrics with Tunable Oleophobicity." Advanced Materials, vol. 21., pp. 1-6. (2009).
Chhatre, Shreerang S., et al., "Scale Dependence of Omniphobic Mesh Surfaces," Langmuir Article, vol. 26, No. 6, pp. 4027-4035 (2010).
Young, Thomas, "An Essay to the Cohesion of Fluids," Philosophical Transactions of the Royal Society of London, vol. 95, pp. 65-87. (1805).
Shirtcliffe, Neil J. et al., "Porous Materials show Superhydrophobic to Superhydrophilic Switching," Chemical Communication, pp. 3135-3137. (2005).
Choi, Wonjae et al., "A Modified Cassie-Baxter Relationship to Explain Contact Angle Hysteresis and Anisotrophy on Non-wetting Textured Surfaces," Journal of Colloid and Interface Science, vol. 339. pp. 208-216. (2009).
Howarter, John A. et al., "Amphiphile grafted Membranes for the Separation of Oil-in-Water Dispersions," Journal of Colloid and Interface Science, vol. 329. pp. 127-132. (2009).
Final Office Action regarding U.S. Appl. No. 14/013,600, dated Feb. 4, 2016.
Kwon, Gibum et al., 'On-demand separation of oil-water mixtures', Advanced Materials, Jun. 12, 2012, vol. 24, Issue 27, pp. 3666-3671.
The International Search Report and Written Opinion of the International Searching Authority dated Feb. 28, 2012 for PCT International Application No. PCT/US2011/40353 (Pub. No. WO 2011/15699).
Nishi, K. et al. "Potential of Rapeseed Oil as Diesel Engine Fuel," SAE Technical Paper. (2004) (Abstract Only).
Extended European Search Report issued in corresponding European application No. 14851492.0.
Canadian Examiner's Report issued in Canadian Application No. CA2802859 dated Jun. 29, 2017.
The International Preliminary Report on Patentability dated Apr. 12, 2016 for PCT International Application No. PCT/US2014/059727 (Pub. No. WO 2015/054406).

(56) References Cited

OTHER PUBLICATIONS

Non-Final Office Action issued in cross-referenced U.S. Appl. No. 12/599,465, dated Dec. 12, 2017.
Owen, Michael J., and Hideki Kobayashi. "Surface active fluorosilicone polymers." *Macromolecular Symposia*. vol. 82. No. 1. Hüthig & Wepf Verlag, 1994.
Canadian Office Action dated Feb. 22, 2018 in corresponding Canadian Application No. 2,802,859.
Boban, Mathew et al., "Smooth, All-Solid, Low-Hysteresis, Omniphobic Surfaces with Enhanced Mechanical Durability," ACS Appl. Mater. Interfaces 2018, 10, pp. 11406-11413 (Published Mar. 19, 2018); DOI: 10.1021/acsami.8b00521.

APPARATUSES AND METHODS FOR ENERGY EFFICIENT SEPARATIONS INCLUDING REFINING OF FUEL PRODUCTS

CROSS-REFERENCE TO RELATED APPLICATIONS

This application is a continuation of U.S. Non-Provisional application Ser. No. 15/027,983 filed on Apr. 7, 2016, which is a National Stage of PCT/US2014/059727, filed on Oct. 8, 2014 that claims the benefit of U.S. Provisional Application No. 61/888,557, filed on Oct. 9, 2013. The entire disclosures of each of the above applications are incorporated herein by reference.

GOVERNMENT RIGHTS

The invention described herein may be manufactured and used by or for the Government of the United States for all governmental purposes without the payment of any royalty.

FIELD

The present disclosure relates generally to methods and apparatuses for liquid-liquid extractions and separations, including separations for refining of fuel.

BACKGROUND

This section provides background information related to the present disclosure, which is not necessarily prior art.

Separation operations span across many manufacturing industries and account for annual energy consumption of 4,500 trillion BTU/year of energy, which is about a quarter of all in-plant energy use in the United States. Fuel separations account for a significant portion of this energy consumption. Equipment for power generation, motor vehicle operation, or reusable rocket operations often require liquid fuels that must meet strict chemical composition specifications in order to satisfy numerous safety, service lifetime, environmental, and regulatory criteria. For example, sulfur content in most liquid fuels used in the United States is tightly controlled in order to, among other reasons, enable the operation of emissions control equipment containing catalysts that are poisoned by sulfur compounds. In addition, many types of modern engines are sensitive to levels of aromatic or nitrogen-containing impurities in liquid fuels due to the build-up of solid residues on critical surfaces, which is believed to be highly accelerated in the presence of these impurities.

Some methods have been developed to remove impurities from fuel feedstock streams, such as hydrodesulfurization ("HDS"), which requires large scale chemical processing equipment for contacting multiple liquid phases, including distillation columns, high-pressure reaction vessels, or large vessels, all of which are highly energy intensive. Furthermore, in certain scenarios, such as after a major natural disaster, these large-scale refineries may be off-line or otherwise unable to provide the refined fuels, which are needed for operation of equipment (including emergency response vehicles and generators) for an extended period of time.

More recent technological advances in fuel refining have not yet been fully implemented into conventional practice for at least two reasons. First, many processes remove both sulfur and aromatic compounds; however, the aromatic content of fuels must often be preserved for compatibility with engine seals and other key system components. Second, large quantities of spent extract are often generated—whereas a highly mobile refinery must otherwise function by recycling at least a small quantity of initially supplied extractant.

As a result, there exists a continuing need for processes to economically, efficiently, and reliably remove impurities from feed streams, especially from liquid fuel feedstocks. This is especially difficult where the one or more impurities to be separated from the feed stream are miscible with the other components in the feed stream. The greatest opportunities for energy savings in separation of miscible components lie in replacing high-energy operations (e.g., distillation) with low-energy alternatives (e.g., extraction). In extraction, one of the primary design challenges is to maximize the interfacial area between the feed and the extractant for efficient mass transfer. This is typically accomplished by energy-intensive techniques such as ultrasonication or pumping the feed and the extractant through columns with moving internals or through packed columns with high tortuosity (which display high resistance to fluid flow). A relatively less energy-intensive technique, primarily used in microfluidic extraction, is emulsification of the feed and the extractant. While emulsions, especially those stabilized by surfactants, provide a large interfacial area and greatly enhance the mass transfer in extraction, the subsequent separation of the extract phase (typically the desirable phase) and the raffinate phase (typically the undesirable phase) can be energy-intensive and less economical.

Consequently, there is a great need and a significant opportunity to develop new energy-efficient extraction methodologies with enhanced mass transfer. There, thus, remains a need for simplified separations processes, including fuel refining processes, that are highly effective and energy efficient, thus not requiring large-scale chemical processing equipment, and that can be accomplished via mobile platforms.

SUMMARY

This section provides a general summary of the disclosure and is not a comprehensive disclosure of its full scope or all of its features.

In various aspects, the present teachings provide methods and devices for low energy consumption, efficient, liquid-liquid extraction or separations. In this manner, the present teachings overcome the foregoing problems and other shortcomings, drawbacks, and challenges of conventional, large-scale, energy intensive separation processes, for example, in fuel refineries. While the inventive technology will be described in connection with certain embodiments, it will be understood that the inventive technology is not limited to these listed embodiments. To the contrary, the inventive technology includes all alternatives, modifications, and equivalents as may be included within the spirit and scope of the present teachings.

In certain aspects, the present disclosure contemplates methods of separating components in a liquid. One such method may comprise an extraction process where an emulsion is created by combining a feed stream, an extractant, and a surfactant. The feed stream may comprise a plurality of distinct components, including a first component present at an initial amount. The first component is to be separated from the feed stream during the extraction process. In certain variations, the feed stream is selected from a group consisting of: a hydrocarbon feed stream (e.g., a fuel or a biofuel) and an azeotrope. The method may further include removing (e.g., extracting) the first component from the emulsion by contacting the emulsion with a superoleophobic and hygroscopic membrane filter. In certain variations, the contacting may facilitate passage of the first component and extractant through the superoleophobic and hygroscopic membrane filter. Then, a purified product is collected that has the desired portion of the first component removed. In certain aspects, the process separates greater than or equal to about 99 weight % of the initial amount of the first component from the feed stream.

According to another aspect of the present disclosure, a method of refining fuels includes selectively removing (e.g., extracting) chemical components in a first phase into a second phase, separating the first and second phases by superoleophobic hygroscopic membrane filters, and, optionally, selective adsorbing extracted components and recycling of extractant into contact with the fuel feed stock or stream. The methods and apparatus contemplated herein enable refining operations, such as removal of nitrogen-containing compounds, desulfurization, and extraction of aromatics without the need for distillation.

In certain aspects, the present disclosure provides a method of refining fuel that comprises combining a fuel feed stream with an extractant to form an admixture. The fuel feed stream comprises a first component present at an initial amount. The method further includes selectively removing (e.g., extracting) the first component and the extractant from the fuel feed stream by contacting the admixture with a superoleophobic and hygroscopic membrane filter that facilitates passage of the first component and extractant through the superoleophobic and hygroscopic membrane filter. The method thus forms a refined fuel having less than or equal to about 1%, by weight, of the first component.

In other aspects, the present disclosure provides a method of refining fuel that comprises introducing a fuel into a contacting vessel to mix the fuel with a continuous phase of an extraction fluid. The method further includes selectively removing (e.g., extracting) the extraction fluid from the contacting vessel. The fuel is coalesced within the contacting vessel and then the coalesced fuel is collected.

In one aspect, a liquid-liquid separation apparatus is provided that comprises a contacting vessel having an extraction fluid disposed therein, or introduced thereto, and a first fluid path fluidically coupled to the contacting vessel. A first inlet is configured to introduce a feed stream, having therein a first component to be extracted, into the extraction fluid in the contacting vessel. A superoleophobic, hygroscopic membrane filter is positioned along the first fluid path, where the superoleophobic hygroscopic membrane filter is selectively permeable to the extraction fluid having the first component therein.

In yet other aspects, an apparatus for liquid-liquid separation is contemplated. Such an apparatus comprises a contacting vessel. A first fluid path is fluidically coupled to the contacting vessel and configured to circulate an extraction fluid. A second fluid path is configured to introduce a feed stream into the contacting vessel, wherein the feed stream comprises a first component. A superoleophobic and hygroscopic membrane filter is positioned within the first fluid path. The superoleophobic and hygroscopic membrane filter is selectively permeable to the extraction fluid and the first component, but selectively impermeable to a purified product. The purified product has the portion of the first component removed and thus comprises a remainder of the feed stream components. A third fluid path fluidically is coupled to the contacting vessel and configured to remove the purified product from the contacting vessel.

In another aspect, a fuel refining apparatus is provided that comprises a contacting vessel having an extraction fluid disposed therein or introduced thereto, a first fluid path fluidically coupled to the contacting vessel, a first inlet configured to introduce a fuel into the extraction fluid in the contacting vessel, and a superoleophobic, hygroscopic membrane filter positioned along the first fluid path. The superoleophobic hygroscopic membrane filter is selectively permeable to the extraction fluid.

In yet another aspect, a fuel refining apparatus is provided that comprises a contacting vessel having an extraction fluid disposed therein. The apparatus has a first fluid path and a second fluid path, each fluidically coupled to the contacting vessel. A stationary absorbent may be positioned between the first and second fluid paths and is configured to selectively absorb at least one impurity from the extraction fluid. A superoleophobic, hygroscopic membrane filter is positioned along the first fluid path, where the superoleophobic hygroscopic membrane filter is selectively permeable to the extraction fluid. A first inlet is in fluid communication with the contacting vessel and configured to introduce a fuel into the extraction fluid in the contacting vessel and a second nozzle is coupled to the second fluid path and configured to introduce the extraction fluid into the contacting vessel.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

Further areas of applicability will become apparent from the description provided herein. The description and specific examples in this summary are intended for purposes of illustration only and are not intended to limit the scope of the present disclosure.

DRAWINGS

The accompanying drawings, which are incorporated in and constitute a part of this specification, illustrate embodiments of the present invention and, together with a general description of the invention given above, and the detailed description of the embodiments given below, serve to explain the principles of the present disclosure.

The drawings described herein are for illustrative purposes only of selected embodiments and not all possible implementations, and are not intended to limit the scope of the present disclosure.

Figures 4A, 4B, 4C:
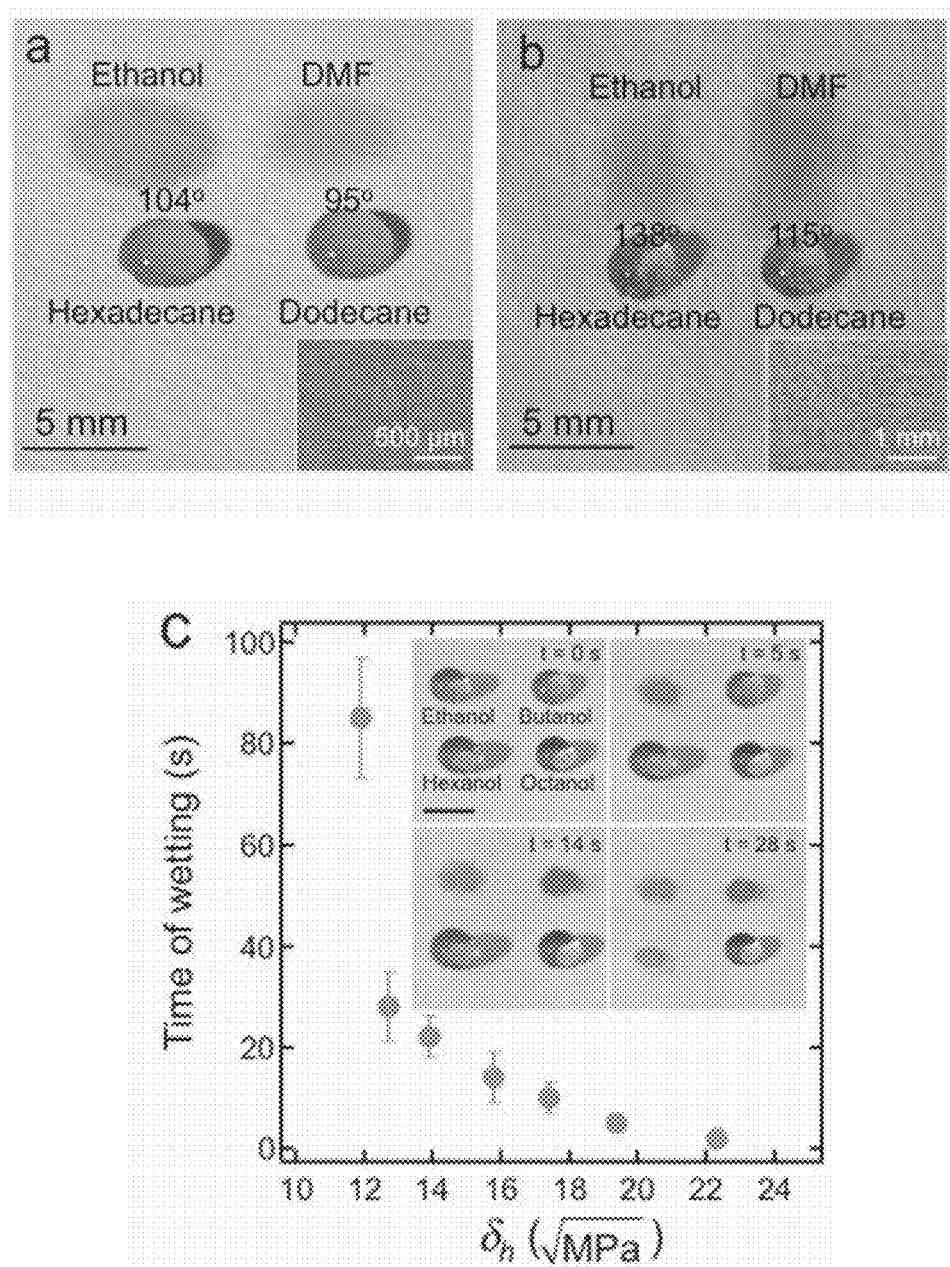

FIGS. 4A-4C: FIGS. 4A-4B show droplets of ethanol (dyed blue), DMF (dyed green), hexadecane (dyed red), and dodecane (dyed yellow) on two distinct superoleophobic, hygroscopic smart membranes prepared in accordance with certain aspects of the present disclosure, for example, fabricated using a filter paper (pore size of 2.5 μm) and a wipe, respectively. The insets of FIGS. 4A-4B show the morphologies of the respective filter paper and wipe surfaces. FIG. 4C graphically illustrates time of wetting (s) for a series of alcohols on the superoleophobic, hygroscopic smart membrane shown in FIG. 4A. Insets within FIG. 4C show sequential wetting of four alcohol droplets in the order of decreasing Hansen hydrogen bonding parameter. Scale bar is 5 mm.

Figure 5:
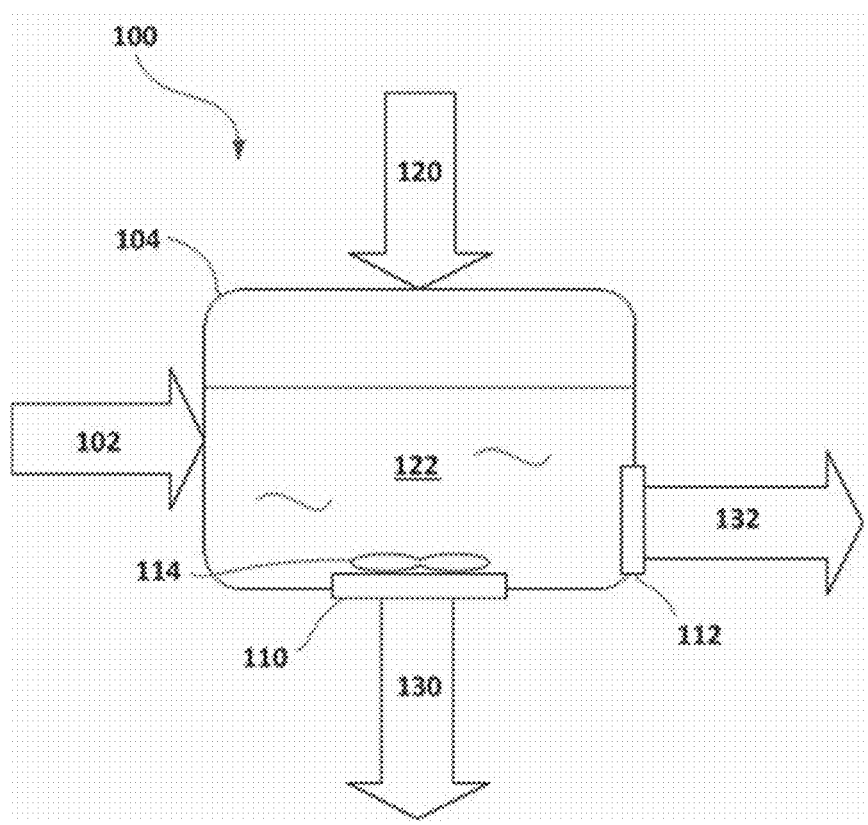

FIG. 5 is a schematic of an exemplary single unit operation extraction apparatus that provides continuous emulsification and separation of at least one component from a feed stream.

Figures 6A, 6B, 6C:
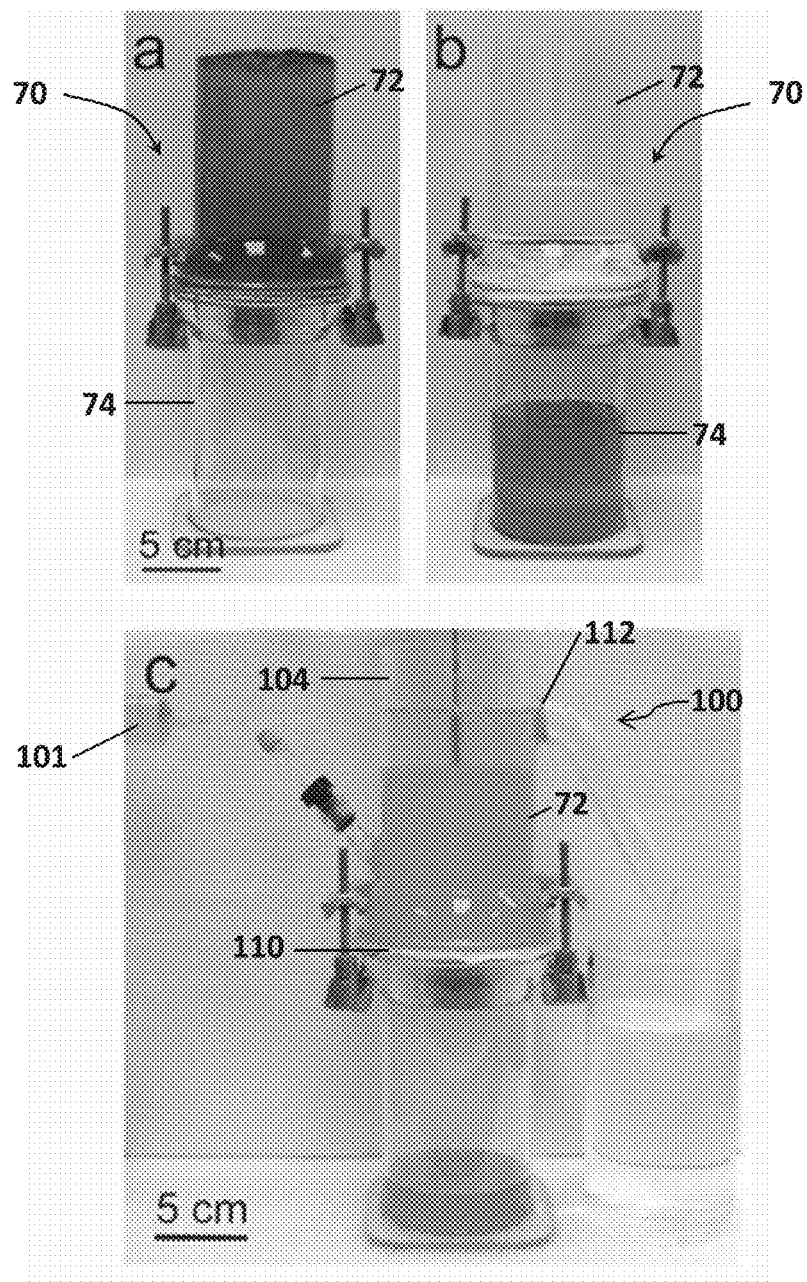
Figures 6D, 6E:
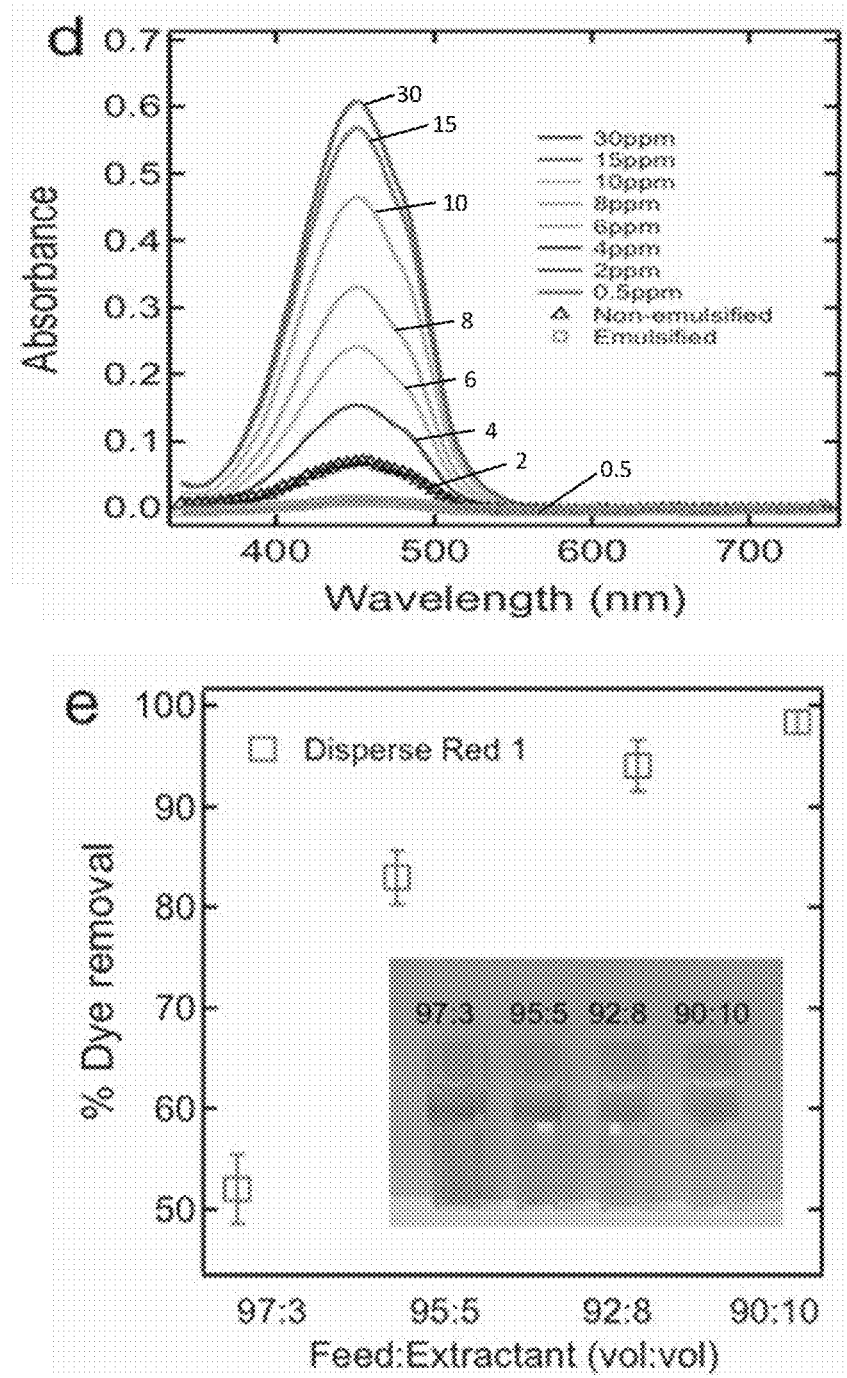

FIGS. 6A-6E: FIG. 6A shows a batch separation apparatus with 50:50 v:v dodecane-in-DMF emulsion above the superoleophobic, hygroscopic smart membrane filter prepared in accordance with certain aspects of the present disclosure. FIG. 6B shows that dye-enriched DMF phase permeates through, while dye-depleted dodecane phase is retained above, the membrane. FIG. 6C shows a continuous separation apparatus for continuous surfactant-enhanced extraction and smart membrane-based separation of dodecane-in-DMF emulsion. The dye-enriched DMF phase continuously passes through the smart membrane at the bottom, while the dye-depleted dodecane phase passes through the conventional membrane on the side-wall. FIG. 6D shows UV-Vis absorbance data for the dye-depleted dodecane phase obtained with and without surfactant-enhanced extraction. Also included is the data for the calibration samples. FIG. 6E shows a percentage dye removal from dodecane using different dodecane:DMF volumetric flow rate ratios. The inset of FIG. 6E shows the dodecane-rich phase after separation.

Figures 7A, 7B, 7C:
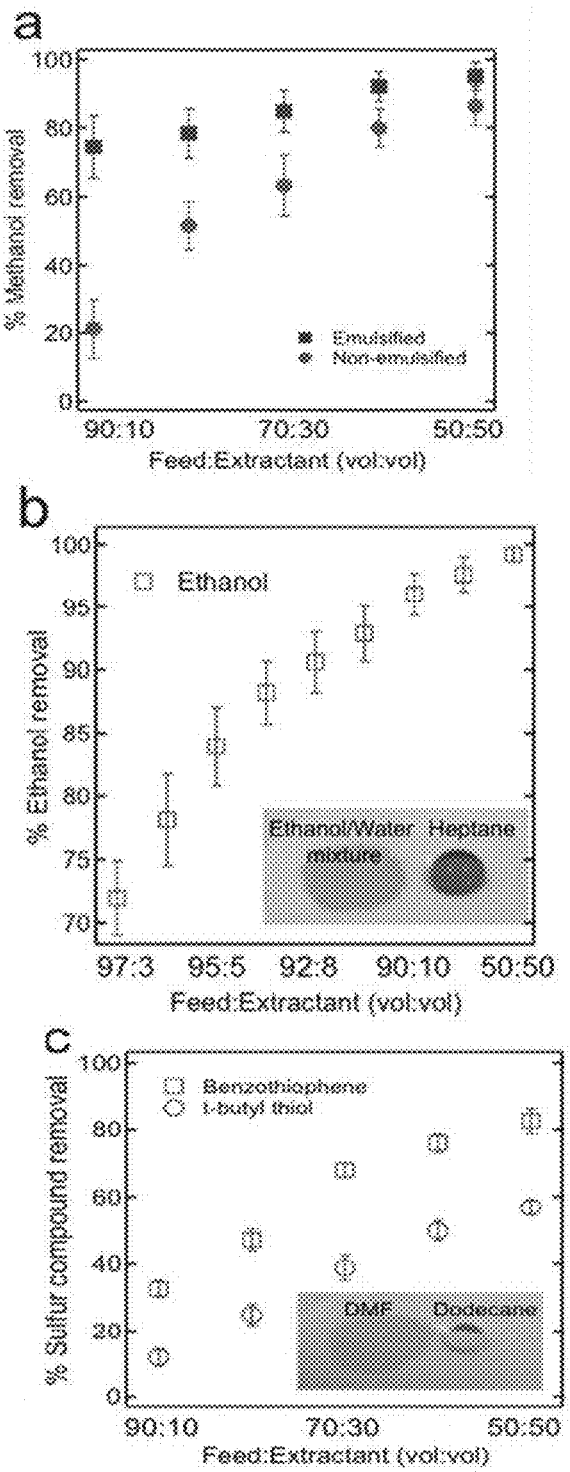

FIGS. 7A-7C: FIG. 7A graphically illustrates a percentage methanol removal from methyl oleate obtained with and without surfactant-enhanced extraction using different methyl oleate:water volumetric flow rate ratios. FIG. 7B graphically illustrates a percentage ethanol removal from ethanol-heptane azeotrope (feed) using different azeotrope:water volumetric flow rate ratios. FIG. 7C graphically illustrates a percentage sulfur compound removal from dodecane using different dodecane:DMF volumetric flow rate ratios. Insets of FIGS. 7B and 7C show the wetting behavior of the polar liquid and the non-polar in each separation on a smart membrane fabricated using a filter paper (pore size of 2.5 µm), respectively.

Figures 8A, 8B, 8C:
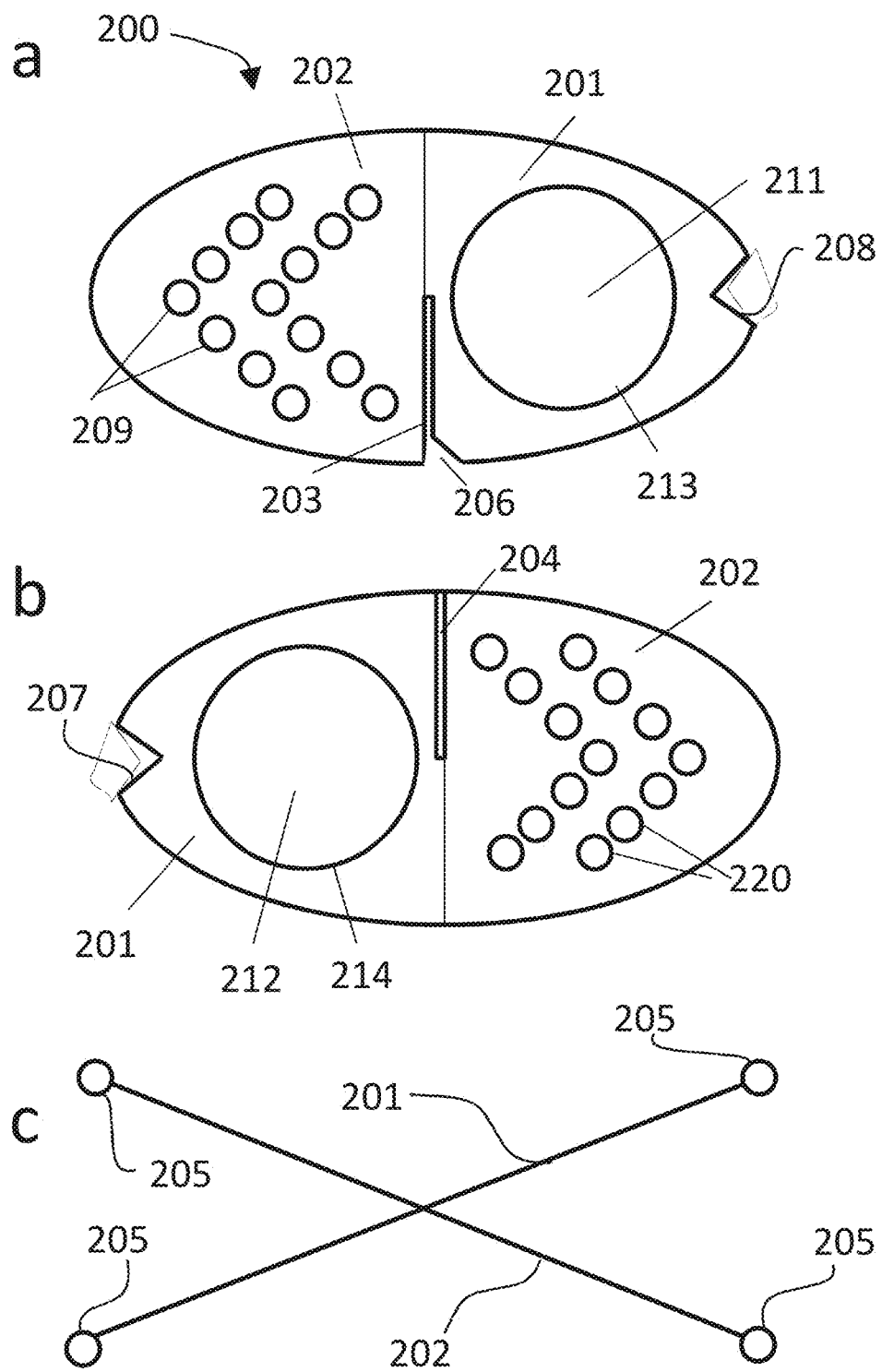

FIGS. 8A-8C: FIG. 8A is a top view of a separator plate assembly for use in a separator apparatus according to certain aspects of the present disclosure. FIG. 8B is a bottom view of the assembly of FIG. 8A. FIG. 8C is a side view of the assembly shown in FIGS. 8A-8B.

It should be understood that the appended drawings are not necessarily to scale, presenting a somewhat simplified representation of various features illustrative of the basic principles of the disclosure. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

Corresponding reference numerals indicate corresponding parts throughout the several views of the drawings.

DETAILED DESCRIPTION

Exemplary embodiments are provided so that this disclosure will be thorough, and will fully convey the inventive scope to those who are skilled in the art. Numerous specific details are set forth, such as examples of specific compositions, components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some exemplary embodiments, well-known processes, well-known device structures, and well-known technologies are not described in detail.

The terminology used herein is for the purpose of describing particular embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected, or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various steps, elements, components, regions, layers, and/or sections, these steps, elements, components, regions, layers, and/or sections should not be limited by these terms, unless otherwise indicated. These terms may be only used to distinguish one step, element, component, region, layer or section from another step, element, component, region, layer, or section. Terms such as "first," "second," and other numerical terms, when used herein, do not imply a sequence or order unless clearly indicated by the context. Thus, a first step, element, component, region, layer, or section discussed below could be termed a second step, element, component, region, layer, or section without departing from the teachings of the exemplary embodiments.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

It should be understood for any recitation of a method, composition, device, or system that "comprises" certain steps, ingredients, or features, that in certain alternative variations, it is also contemplated that such a method, composition, device, or system may also "consist essentially of" the enumerated steps, ingredients, or features, so that any other steps, ingredients, or features that would materially alter the basic and novel characteristics of the invention are excluded therefrom.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about," whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters.

In addition, disclosure of ranges includes disclosure of all values and further divided ranges within the entire range, including endpoints and sub-ranges given for the ranges.

Exemplary embodiments will now be described more fully with reference to the accompanying drawings.

The present disclosure contemplates new energy-efficient extraction methodologies with enhanced mass transfer and devices for conducting the same. In certain aspects, the present disclosure provides a single unit operation that uniquely combines two processes together. First, an extraction process may be employed using surfactant-stabilized emulsions that is highly effective and, second, is energy efficient in that it may be a solely-gravity driven (i.e., without any external energy) separation process for liquid-liquid mixtures or emulsions using smart superoleophobic, hygroscopic membrane filters in accordance with certain aspects of the present disclosure. It should be noted that the use of the terms "smart membranes," "smart filters," and "superoleophobic, hygroscopic membrane filters" are used interchangeably herein. In this manner, such techniques can be used to separate miscible components from admixtures or emulsions of multiple components down to a purity of only a few ppm (e.g., less than 50 ppm). Such methods can be used in a variety of separation and liquid-liquid extraction processes, including for refining hydrocarbon streams, like fuels, such as producing diesel with ultra-low sulfur content, separations and recovery of bio-fuels, removal of dyes from jet fuels, as well as separation of azeotropes, by way of non-limiting examples.

Smart membrane filters can be formed as discussed herein and possess hygroresponsive surfaces (e.g., surfaces that respond to the contacting liquid). Such hygroresponsive surfaces can be considered to reversibly turn superhydrophilic when contacted by water or polar liquids, but are able to sustainably maintain oleophobicity both in air and when submerged under liquids and water. Generally, surfaces that display contact angles ($\theta$) greater than about 90° with water are considered to be hydrophobic, and surfaces that display $\theta$ greater than 90° with oil are considered to be oleophobic. Notably, the use of "hydro" nomenclature is intended to encompass both water and polar liquids, while "oleo" nomenclature encompasses non-polar liquids, including oils.

Surfaces that spontaneously approach $\theta$ values of 0° with water are generally considered superhydrophilic and 0° with oil are superoleophilic, respectively, and surfaces that approach $\theta$ values greater than about 150° and having a low contact angle hysteresis (difference between the advancing $\theta_{adv}$ and the receding contact angle $\theta_{rec}$) with water and oil are generally considered to be superhydrophobic and superoleophobic, respectively.

In certain aspects, the present disclosure uses superoleophobic, hygroscopic membrane filters that may be considered to be superoleophobic and hydrophilic or superhydrophilic. As noted above, oleophobic surfaces are those that have an apparent advancing contact angle of greater than or equal to about 90° for preselected low surface tension liquids. Superoleophobic surfaces are those that display a contact angle of greater than or equal to about 150°, optionally greater than or equal to about 151°, optionally greater than or equal to about 152°, optionally greater than or equal to about 153°, optionally greater than or equal to about 154°, optionally greater than or equal to about 155°, optionally greater than or equal to about 156°, optionally greater than or equal to about 157°, optionally greater than or equal to about 158°, optionally greater than or equal to about 159°, and in certain aspects, optionally greater than or equal to about 160° along with a low contact angle hysteresis (difference between the advancing $\theta_{adv}$ and the receding contact angle $\theta_{rec}$) with preselected low surface tension liquids, such as a representative oil (for example, rapeseed oil (RSO)). In certain variations, a "superoleophobic" surface has a contact angle of greater than or equal to about 150° and less than or equal to about 180° with a preselected oil, like representative RSO.

Surfaces that display a contact angle of less than or equal to about 90°, optionally of less than or equal to about 85°, optionally of less than or equal to about 80°, optionally of less than or equal to about 75°, optionally of less than or equal to about 70°, optionally of less than or equal to about 65°, optionally of less than or equal to about 60°, optionally of less than or equal to about 55°, optionally of less than or equal to about 50°, and in certain aspects, optionally of less than or equal to about 45° with water or other polar liquids (e.g., alcohols, dimethyl formamide and the like) are considered to be "hydrophilic."

As used herein, surfaces that display a contact angle of less than or equal to about 5°, optionally of less than or equal to about 4°, optionally of less than or equal to about 3°, optionally of less than or equal to about 2°, optionally of less than or equal to about 1°, and in certain aspects, 0° with water or other polar liquids (e.g., alcohols, dimethyl formamide and the like) are considered to be "superhydrophilic."

Thus, when a non-polar liquid (virtually any oil) droplet contacts a smart membrane filter according to certain aspects of the present disclosure, it cannot permeate through and displays a high apparent contact angle ($\theta^*$). For example, the advancing apparent contact angles for hexadecane and dodecane are $\theta^*_{adv}$ is 104° and $\theta^*_{adv}$ is 95°, respectively, on a smart membrane fabricated using a 2.5 µm pore size cellulose-based filter paper (see FIG. 4A) and $\theta^*_{adv}$ is 132° and $\theta^*_{adv}$ is 115°, respectively, on a smart superoleophobic, hygroscopic membrane filter fabricated using a cellulose-based wipe as a porous substrate (see FIG. 4B). This is due to a combination of the re-entrant texture of the membrane and the low surface energy of the perfluorinated groups on the surface. In contrast, when a polar liquid (virtually any protic or aprotic solvent that can hydrogen bond) droplet contacts a superoleophobic, hygroscopic membrane filter, it completely wets the surface and permeates through (see FIGS. 4A-4B). This is due to the hydrogen bonding interactions between the polar liquid and the cellulose-based membrane surface. This is also evident from the dependent decrease time of wetting (i.e., the time required for a polar liquid to imbibe into the membrane) with increasing Hansen hydrogen bonding parameter (see FIG. 4C).

The preferential wetting of such smart superoleophobic, hygroscopic membranes by polar liquids over non-polar liquids can be used to separate mixtures of immiscible polar and non-polar liquids. However, conventionally, the separation of miscible components, such as miscible polar and non-polar liquids, has posed significant challenges and where feasible, has required energy intensive separation techniques. Here, in certain variations, a single unit operation is contemplated that may combine (a) extraction using surfactant-stabilized emulsions and (b) solely-gravity driven separation of these emulsions using smart superoleophobic, hygroscopic membrane filter membranes to separate miscible components.

Thus, in certain aspects, the present disclosure provides a method of separating components in a liquid comprises an emulsion (e.g., a surfactant-stabilized emulsion) by combining a feed stream, an extractant or extraction fluid, and a surfactant. The feed stream may comprise a complex composition comprising a plurality of distinct components, including a first component present at an initial amount. The first component is desirably to be separated or extracted from the feed stream. In certain variations, the feed stream is selected from a group consisting of: a hydrocarbon feed stream and an azeotrope. A hydrocarbon feed stream is intended to include crude, unrefined petroleum-based feed stocks that may be refined to produce hydrocarbon-containing fuels and lubricants, as well as partially or fully refined fuels and lubricants. Examples of hydrocarbon feed streams that can be processed in accordance with the present disclosure include diesel fuel, jet fuel, gasolines (including unleaded motor and aviation gasolines), kerosene, liquid petroleum gas, bunker oils, lubricant oils, low sulfur fuels, coal-derived liquid fuels, ethers, synthetic fuels, alcohols and biofuels (derived from biomass or other natural sources and/or including ethanol), biodiesel, biodiesel-derived fuel, and synthetic diesels.

The extractant or extraction fluid may be a polar composition when the feed stream is a non-polar composition, such as water, an alcohol, or dimethyl formamide, by way of non-limiting example. Oil and water emulsions are created by use of surface-active agents, like surfactants and detergents, that stabilize the dispersed phase in smaller droplets. The hydrophilic-lipophilic balance (HLB) of a surfactant used in a surfactant-stabilized mixture of oil and water can be used to predict the formation of either an oil-in-water or a water-in-oil emulsion. However, depending on the concentration of the dispersed phase and/or the temperature of the system, an oil-in-water emulsion may invert to a water-in-oil emulsion or vice-versa (a water-in-oil emulsion inversion to an oil-in-water emulsion). In addition, as many as three different phases (oil, oil-in-water emulsion or water-in-oil emulsion, and water) may co-exist in oil-water mixtures.

Mixtures of oil and water are separated into three categories based on the average size or diameter of oil droplet ($d_{oil}$), namely a "free oil" if $d_{oil}$ is greater than about 150 micrometers (μm), a "dispersed oil" if $d_{oil}$ is less than about 150 μm and greater than about 20 μm, and an "emulsified oil" if $d_{oil}$ is less than about 20 μm. Thus, in certain aspects, the methods of the present disclosure may form an emulsified oil or emulsion from an admixture of the feed stream and extractant/extraction fluid, which is an emulsion of oil and water, for example, an oil-in-water emulsion (where water is the continuous phase and oil is the dispersed phase) or a water-in-oil emulsion (where oil is the continuous phase and water is the dispersed phase). Various embodiments of the present teachings can likewise be used as membrane separators for other immiscible or miscible component mixtures, such as mixtures of polar and non-polar liquids, or alcohols and alkane mixtures, by way of non-limiting examples.

The method further comprises removing (e.g., extracting) the first component by contacting the emulsion with a superoleophobic and hygroscopic membrane filter that facilitates passage of the first component and extractant through the superoleophobic and hygroscopic membrane filter, so that the contacting separates at least 85 weight % of the initial amount of the first component from the feed stream (i.e., an efficiency of separation that is at least 85 weight %). In certain aspects, the efficiency of separation according to the present teachings is greater than or equal to about 90 weight %, optionally greater than or equal to about 95 weight %, optionally greater than or equal to about 97 weight %, optionally greater than or equal to about 99 weight %, optionally greater than or equal to about 99.5 weight %, optionally greater than or equal to about 99.9 weight %, optionally greater than or equal to about 99.99 weight %, optionally greater than or equal to about 99.999 weight %, and in certain aspects, optionally greater than or equal to about 99.9999 weight %. In certain aspects, the present methods can be used to reduce the amount of the first component to less than or equal to about 1%, by weight, in the refined or purified product after processing, optionally less than or equal to about 1,000 parts per million (ppm, mg/kg, or about 0. 1% by weight), optionally less than or equal to about 100 ppm (about 0.01% by weight), optionally less than or equal to about 50 ppm (about 0.005% by weight), and in certain variations, optionally less than or equal to about 10 ppm (about 0.001% by weight).

The method may further include removing (e.g., extracting) the first component from the emulsion by contacting the emulsion with a superoleophobic and hygroscopic membrane filter that facilitates passage of the first component and extractant through the superoleophobic and hygroscopic membrane filter. In certain aspects, the removing (e.g., extracting) of the first component from the emulsion (and feed stream) can be done where the contacting is conducted by gravity-feeding the emulsion to the superoleophobic and hygroscopic membrane filter at ambient conditions. The removing (e.g., extracting) of the first component by contacting is conducted in a single unit operation, in other words, a single stage separation process. Then, a purified product is collected that has the desired portion of the first component removed. In certain aspects, the process separates a significant portion of the first component from the feed stream. Notably, the contacting with the superoleophobic and hygroscopic membrane filter also separates and breaks the emulsion with only minimal energy expenditure.

In certain aspects, the feed stream comprises a first component and a second component. In certain aspects, the feed stream may comprise a first component, a second component, and at least one additional component (e.g., a third component), where the first and second components are miscible. In other aspects, the first component comprises a polar molecule and the second component comprises a non-polar molecule, where the first and second components may be miscible.

The feed stream may alternatively comprise a plurality of distinct components in addition to the first component, so that the removing (e.g., extracting) the first component by contacting the emulsion with a superoleophobic and hygroscopic membrane filter separates the first component from the plurality of distinct components.

In certain other aspects, the feed stream is a fuel comprising the plurality of distinct components in addition to the first component, where the first component is a contaminant or impurity and the plurality of distinct components are fuel components, so that the removing of the first component by contacting the emulsion with a superoleophobic and hygroscopic membrane filter separates the first component from the fuel components to form a purified fuel.

The present disclosure also contemplates separator devices for continuously conducting such methods in a single unit operation, for example, where the emulsion is gravity fed towards the superoleophobic and hygroscopic membrane filter to continuously separate the first component and the extractant from the emulsion. In certain variations, the separator device may further comprise a second membrane filter that is configured to continuously remove another component (such as one distinct component of the plurality) of the feed stream from a region above the superoleophobic and hygroscopic membrane filter.

According to another aspect of the present disclosure, a method of refining fuels includes selectively removing (e.g., extracting) chemical components from a first phase into a second phase, separating the first and second phases by superoleophobic hygroscopic membrane filters, and, optionally, selective adsorbing extracted components and recycling of extractant into contact with the fuel feed stock or stream. The methods and apparatus contemplated herein enable refining operations, such as removal of nitrogen-containing compounds, desulfurization, and extraction of aromatics without the need for distillation or other separations processes.

In certain aspects, methods of refining fuel are provided that combine a fuel feed stream with an extractant or extraction fluid to form an admixture. The fuel feed stream comprises a first component present at an initial amount. The method further includes selectively removing (e.g., extracting) the first component and the extractant from the fuel feed stream by contacting the admixture with a superoleophobic and hygroscopic membrane filter that facilitates passage of the first component and extractant through the superoleophobic and hygroscopic membrane filter. The selective extraction, thus, preferentially removes or extracts the first component from the admixture of the fuel feed and extractant. In certain variations, the method of refining, thus, forms a refined fuel having less than or equal to about 1%, by weight, of the first component. In certain other aspects, the method of refining fuel may further include introducing a surfactant with the fuel feed stream and the extractant, so that the admixture forms an emulsion prior to selectively removing (e.g., extracting) the first component.

In other aspects, the present disclosure provides a method of refining fuel that comprises introducing a fuel into a contacting vessel to mix the fuel with a continuous phase of an extraction fluid. The fuel is coalesced within the contacting vessel and then the coalesced fuel is collected as a refined and processed fuel product.

In certain aspects, the combining of the fuel feed stream with an extractant may further include introducing (e.g., dispersing) the fuel feed stream into a contacting vessel having a continuous phase of the extractant. The selectively removing (e.g., extracting) further comprises: removing the extraction fluid from the contacting vessel, coalescing the dispersed fuel within the contacting vessel, and collecting the coalesced fuel as the refined fuel. In certain aspects, the refined fuel has less than or equal to about 1,000 ppm of the first component. In other aspects, the refined fuel may be selected from a group consisting of: diesel fuel, jet fuel, gasolines (including unleaded motor and aviation gasolines), kerosene, liquid petroleum gas, bunker oils, lubricant oils, low sulfur fuels, coal-derived liquid fuels, ethers, synthetic fuels, alcohols and biofuels (derived from biomass or other natural sources), ethanol, biodiesel, biodiesel-derived fuel, and synthetic diesels, by way of non-limiting examples.

In accordance with yet another aspect of the present disclosure, an apparatus for separating components in a liquid-liquid extraction process according to the methods described above are contemplated. Likewise, an apparatus for refining fuels according to the methods described above are also contemplated.

In one aspect, a liquid-liquid separation apparatus is provided that comprises a contacting vessel having an extraction fluid disposed therein, a first fluid path fluidically coupled to the contacting vessel, and a first inlet fluidically coupling the fluid path to the contacting vessel and configured to introduce a feed stream into the extraction fluid in the contacting vessel. The feed stream comprises a first component to be extracted. A superoleophobic, hygroscopic membrane filter is positioned along the first fluid path, where the superoleophobic hygroscopic membrane filter is selectively permeable to the extraction fluid having the first component therein.

In another aspect, a fuel refining apparatus is provided that comprises a contacting vessel having an extraction fluid disposed therein, a first fluid path fluidically coupled to the contacting vessel, a first inlet (e.g., nozzle) fluidically coupling the fluid path to the contacting vessel and configured to introduce a fuel into the extraction fluid in the contacting vessel, and a superoleophobic, hygroscopic membrane filter positioned along the first fluid path, the superoleophobic hygroscopic membrane filter being selectively permeable to the extraction fluid.

In yet another aspect, a fuel refining apparatus is provided that comprises a contacting vessel having an extraction fluid disposed therein. The apparatus has a first fluid path and a second fluid path, each fluidically coupled to the contacting vessel. A stationary absorbent may be positioned between the first and second fluid paths and is configured to selectively absorb at least one impurity from the extraction fluid. A superoleophobic, hygroscopic membrane filter is positioned along the first fluid path, where the superoleophobic hygroscopic membrane filter is selectively permeable to the extraction fluid. A first inlet (e.g., nozzle) fluidically couples the first fluid path to the contacting vessel and is configured to introduce a fuel into the extraction fluid in the contacting vessel. A second inlet (e.g., nozzle) fluidically couples the second fluid path to the contacting vessel and is configured to introduce the extraction fluid into the contacting vessel.

Figure 1:
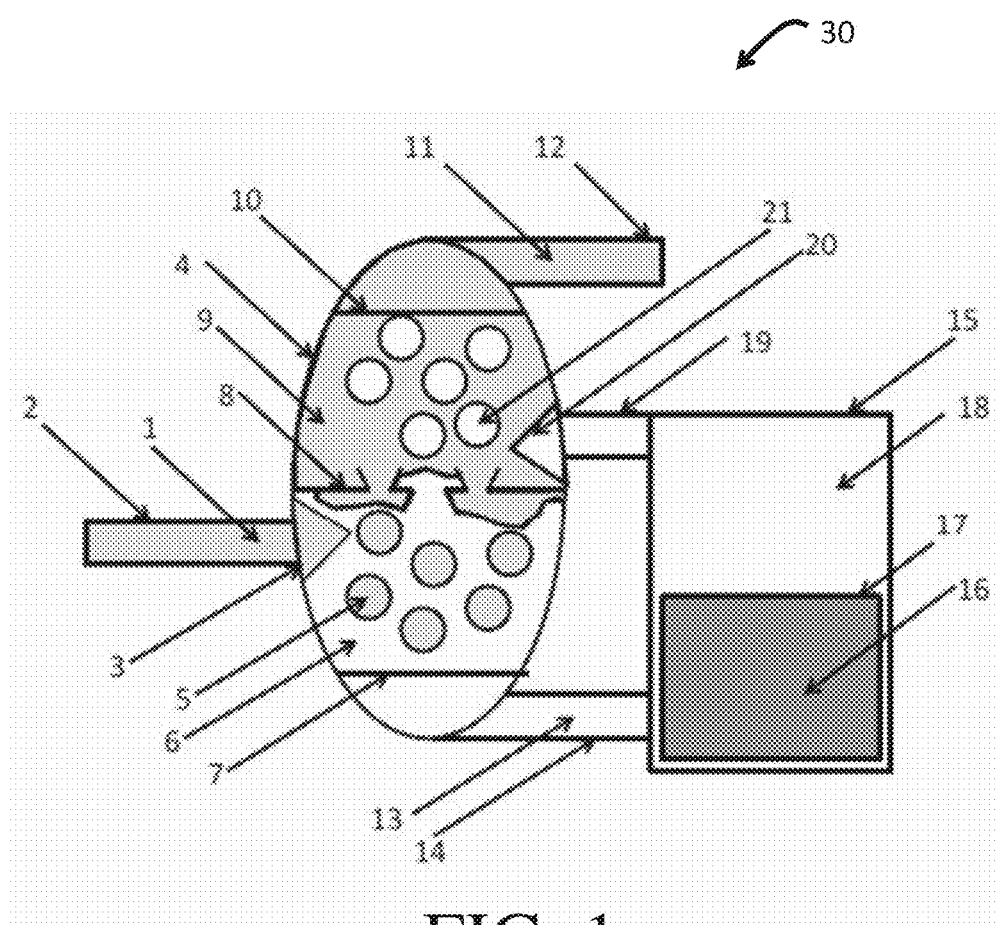
FIG. 1 illustrates one embodiment according to certain aspects of the present disclosure.

With reference to FIG. 1, an apparatus 30 according to one embodiment of the present disclosure is shown and includes a feed stream 1 (e.g., a fuel feedstock) flowing via a conduit or tube 2 to a first spray nozzle 3, which is positioned within a contacting vessel 4. In this variation, for purposes of illustration, apparatus 30 can be considered to be a fuel refining device that separates one or more impurities components from the fuel feedstock (feed stream 1), although, as appreciated by those of skill in the art, is widely applicable to a variety of different separation processes. The flow of the feed stream 1 through openings within the nozzle 3, under pressure, causes the introduction (e.g., dispersion) of the feed stream 1, as droplets 5 (e.g., fuel droplets), into a continuous phase of an extractant or extraction fluid 6 (e.g., a polar extraction fluid). A volume of the extraction fluid 6 may be adjusted so as to maintain complete immersion of the nozzle 3. Notably, a surfactant may also be introduced to the contacting vessel 4, with the extraction fluid 6, to facilitate formation of a surfactant-stabilized emulsion. The surfactant may be introduced with the extraction fluid 6 or the feed stream 1.

The apparatus 30 further includes a first filter 7 (i.e., a superoleophobic, hygroscopic membrane) having selective permeability to the extraction fluid 6 while being impermeable to the fuel droplets 5. According to some embodiments, the first filter 7 may be a membrane constructed in accordance with KOTA, A. K. et al., "Hygro-responsive filters for effective oil-water separation," Nat. Comm. (2012) 3; and KWON, G. et al., "On-Demand Separation of Oil-Water Mixtures," Adv. Mater., Vol. 24 (2012) 3666-3671, which are incorporated herein by reference, in their entireties. Briefly, in certain aspects, such superoleophobic, hygroscopic membrane filters can effectively separate fuels from water and alcohol-containing phases.

The first filter 7 can be formed of a porous material as a substrate. The porous material may be woven or nonwoven, such as fabrics or papers. In certain aspects, the porous material is constructed from one or more materials selected from the group consisting of screen, mesh, paper, woven cloth (e.g., cloth or fabric), non-woven cloth (e.g., felt), fiber, foam, molecular sieves, entangled nanowires, and electrospun polymeric nanofibers, and combinations thereof, by way of non-limiting examples.

In certain aspects, the first filter 7 can be formed by applying at least one low surface energy material to a region of a surface of a porous substrate. In certain variations, a first material and a second distinct material are applied to one or more regions of the substrate. The first material is capable of hydrogen bonding or electrostatically interacting with a polar or charged moiety. The second distinct material is a low surface energy material. Notably, the materials applied to the surface of the porous substrate in such an embodiment may include multiple first and second materials, but may further include additional materials.

Particularly suitable examples of the first material include polymers cross-linked by the inclusion of the diacrylic esters or dimethacrylic esters of ethylene glycol monomers and polymers, such as the acrylates and dimethacrylates of polyethylene glycol, namely, poly(ethylene glycol) diacrylate (PEGDA), or poly(ethylene glycol) dimethacrylate. Other suitable materials include polyvinylpyrrolidone (PVP), which generally refers to a polymer containing vinyl pyrrolidone (also referred to as N-vinylpyrrolidone, N-vinyl-2-pyrrolidione and N-vinyl-2-pyrrolidinone) as a monomeric unit. Yet other suitable hydrophilic polymers include poly(N-isopropyl acrylamide), polyvinylalcohol (PVA), polyepoxysuccinic acid and its salt derivatives, alkylsuccinic polyglyceride, glycerol alkoxylate, polyalkyloxazoline, and poly(allylamine). In yet other aspects, the first material is a charged polymeric material capable of electrostatically interacting with a charged moiety or species, such as a polyelectrolyte.

In certain variations, where the first material and second material are applied, the second material has a low surface energy and may be a silsequioxane derivative. "Silsequioxane" is the general name for a family of polycyclic compounds consisting of silicon and oxygen. Silsequioxanes are also known as silasesquioxanes and polyhedral oligomeric silsesquioxanes ("POSS"). In certain variations, a particularly preferred second material comprises 1H, 1H, 2H, 2H-heptadecafluorodecyl polyhedral oligomeric silsequioxane (F-POSS=8 mN/m). In certain aspects, the addition of F-POSS leads to a rapid reduction in the overall surface energy of the porous substrate (for example, to an estimated $\gamma_{sv}$=10 mN/m). Other suitable second low surface energy materials are those having a surface energy of less than or equal to about 25 mN/m, and in certain variations, a surface energy of greater than or equal to about 6 mN/m to less than or equal to about 25 mN/m at standard pressure and temperature conditions.

In certain alternate variations, such materials include, by way of non-limiting example, graphite fluoride or organofluorine compounds (such as perfluorodecanethiol), polytetrafluoroethylene, fluorosurfactants, fluorosilanes, derivatives, and combinations thereof. Thus, in certain variations, the second material is optionally selected from the group consisting of: 1H, 1H, 2H, 2H-heptadecafluorodecyl polyhedral oligomeric silsequioxane (F-POSS), perfluorodecyl trichlorosilane and perflourodecyl dimethyl chlorosilane, graphite fluoride, perfluorodecanethiol, derivatives, and combinations thereof. Other materials that provide very low surface energies known or to be discovered by those of skill in the art are likewise contemplated.

A ratio of the first material to the second material in the precursor may vary depending upon the application; however, in certain embodiments, a weight ratio of the first material to the second material may be 100:1 to 1:100; optionally from 10:1 to 1:10; optionally from 7:1 to 3:1; and in certain aspects, optionally from 5:1 to 4:1.

In certain variations, the superhydrophilic and superoleophobic membrane filter is coated with a cross-linked material formed from a hydrophilic polymer comprising poly (ethylene glycol) diacrylate (PEDGA), a low surface energy material comprising 1H, 1H, 2H, 2H-heptadecafluorodecyl polyhedral oligomeric silsequioxane (F-POSS), and a cross-linker comprising 2-hydroxy-2-methyl propiophenone.

In certain other variations, the porous substrate can be treated by reacting with a low surface energy silane component (as noted above) to form a surface coating thereon and without need for applying the first material. The silane component is selected to have a low surface energy, which may be less than or equal to about 25 mN/m. Suitable low surface energy fluoroalkyl silanes may have one or more hydrolyzable ligands complexed to an Si atom. In certain aspects, a particularly suitable low surface energy fluoroalkyl silane is a perfluoroalky silane, heptadecafluoro-1,1, 2,2-tetrahydrodecyl triethoxysilane, by way of non-limiting example.

After the low surface energy material is applied to the surface of the porous substrate, the region to which the surface energy material is applied is rendered both superhydrophilic and oleophobic. In yet other variations, after the low surface energy materials are applied to the surface of the porous substrate, the region to which the surface energy material is applied is rendered both superhydrophilic and superoleophobic.

With renewed reference to FIG. 1, intimate contact between the droplets 5 and the extraction fluid 6 causes selective extraction of impurities from the feed stream 1. Thus, contact of fuel droplets 5 and extraction fluid 6 causes differential transfer of chemical components (e.g., impurities) from the feed stream 1 (e.g., fuel feedstock) and fuel droplets 5 to the extraction fluid 6, in accordance with differences in chemical potential between the phases and the kinetics of mass transfer. Because the first filter 7 is impermeable to the droplets 5, the droplets 5 accumulate within the contacting vessel 4 and, upon reaching a critical mass, coalesce. Optionally, coalescence may be aided with one or more stage separator plates 8 that are configured to form a separate continuous phase 9.

According to some embodiments of the present disclosure, a difference in density between the fuel phase of the droplets 5 and the phase of the extraction fluid 6 may further aid in coalescence. More particularly, the continuous fuel phase 9 may contact a second membrane filter 10, which may be a hydrophobic/oleophilic filter, which is selectively permeable to passage of the continuous fuel phase 9 but not the extraction fluid 6. A refined fuel phase 11 passes through the second filter 10 and is collected by flowing out of the device 30 via a collection conduit or tube 12.

Alternatively, and during sufficiently slow rates of operation having a sufficient difference in density between the phases, the continuous fuel phase 9 may sufficiently coalesce into the refined fuel phase 11 and may be collected through the tube 12 without the need for the second filter 10. According to this alternative embodiment, a simple fuel outlet port (not shown) may be incorporated for monitoring and preventing passage of extraction fluid 6, and is operable as the second hydrophobic/oleophilic filter 10.

Extraction fluid 6 that has passed through the first filter 7, i.e., extracted fluid 13, passes through an extract tube 14 to an optional adsorption vessel 15. Within the adsorption vessel 15, the extracted fluid 13 may pass through a stationary adsorbent 16, which may be prevented from becoming entrained in the extract fluid flow by means of a porous confinement 17. The stationary adsorbent 16 is configured to trap, via physical or chemical reaction, selected chemical compounds or impurities present in the extracted fluid 13.

After passing through the stationary adsorbent 16, the now selectively cleaned, extracted fluid 18 may pass through an extraction fluid feed conduit or tube 19 and return to the contact vessel 4. A spray nozzle 20 coupled to the extraction fluid feed tube 19 introduces the selectively cleaned, extracted fluid 18 as dispersed extract droplets 21 into the continuous phase 9. Volumes of the interphase between the extraction fluid 6 and the continuous phase 9 may be adjusted to ensure that the spray nozzle 20 is continuously immersed within the continuous phase 9.

As noted above, the extract droplets 21 are unable to pass through the second filter 10 and, thus, coalesce. Coalescence may be aided by the optional presence of one or more stage separators 8, by a difference in density between the continuous phase 9 and the dispersed extract droplets 21, or both. The coalesced extraction fluid 6 may be maintained around the fuel spray nozzle 3, as described previously. In this way, the extraction fluid 6 may flow in a continuous loop between and through the contacting vessel 4 and the adsorption vessel 15.

The selectively cleaned, extracted fluid 18, whether dispersed as droplets 21 or coalesced as extraction fluid 6, will, after sufficient residence time in contact with a fuel feedstock of constant composition, accumulate impurities. Accumulation, more particularly, occurs as the chemical potential of the impurities approaches equilibrium in both the feed stream 1 and the extraction fluid 6 phases. As a result, continuous extraction of these non-adsorbed impurities does not take place.

Only adsorbed impurities are continuously extracted from the fuel feedstock 1 and accumulate in the stationary adsorbent 16. In particular, when the stationary adsorbent 16 is designed so as to allow adsorption via chemical reaction of selected impurities, the capacity of the stationary adsorbent 16 for the chemically-reacted impurities is increased by orders of magnitude as compared to adsorption via physical trapping at surfaces. Accordingly, embodiments of the present disclosure enable selective extraction of impurities on the basis of reactivity with the stationary adsorbent 16 as opposed to solubility in the extraction fluid 6, as in conventional liquid-liquid extraction processes.

Moreover, chemical reactivity of the stationary adsorbent 16 may depend on the extracted fluid 13 in which the adsorption occurs (see, for instance, LANDAU, M. V. et al., "Ultradeep adsorption-desulfurization of gasoline with Ni/Al—$SiO_2$ material catalytically facilitated by ethanol," Ind. Eng. Chem. Res., Vol. 47 (2008) 6904-6916, incorporated by reference herein). Thus, use of a combined extraction-adsorption process enables selection of the extracted fluid 13, in addition to the fuel feedstock 1, so as to maximize a rate of chemical reaction in the stationary adsorbent 16.

Although not specifically shown, according to some embodiments of the present disclosure, the extract feed conduit or tube 19 may be coupled to a separate vessel containing a fresh supply of extraction fluid 6. As such, the extracted fluid 13 may be collected and discarded or be passed through stationary adsorbent 16 before collection and/or discarding. Such open-loop embodiments of the present disclosure may still effect the selective removal of impurities based on differences in chemical potential between a given impurity in a fuel feedstock and the supplied extraction fluid 6, but may also be useful in testing the operation of the extraction-related portions of the apparatus 30, independently of the adsorption-related portions.

According to some embodiments of the invention, the separator plate 8 may be an assembly. FIGS. 8A-8C show an example of one such assembly 200. In some embodiments, from two to one thousand of the assemblies shown in FIGS. 8A-8C are stacked one on top of another, with each successive element rotated horizontally by 180° with respect to the neighboring assembly, and with all assemblies contained in the tube 2 of FIG. 1. Multiple views of the design of the assembly are depicted in FIGS. 8A-8C. FIG. 8A is a top view of separator assembly 200, FIG. 8B is a bottom view, and FIG. 8C is a side view of the separator assembly 200. The example separator plate assembly 8 is formed by two stainless steel plates 201 and 202. Each plate contains a central slot 203 for plate 201, and 204 for plate 202, which allows the two plates 201 and 202 to be fastened together in the form of a butterfly. The plates 201 and 202 of the assembly are design to rest at opposite angles within the tube. A loose seal with the inner wall of the tube 2 is formed by means of slitted Santoprene O-rings 205 that fit over the edges of the plates 201 and 202. Example dimensions for the plates 201 and 202 include a thickness of 1 mm, a maximum length of 152.9 mm and a maximum width of 131.9 mm.

The plate 202 contains a central aperture 206 and two edge apertures 207 and 208, which permit the free flow of fluid through the plate at a small rate for the purpose of removing fluids that may become trapped at the upper or lower extremities of the sectioned spaces within the tube created by insertion of the assembly. An example form of these apertures is a triangular notch having sides of 2.5 mm in length. The plate 202 contains perforations 209 and 210 that disperse fluid passing through into small drops. An example form for each perforation is a circular hole 1 mm in depth and 1 mm in diameter, machined so that the entrances on the top sides of the perforations 209 are smooth, while those on the bottom side are smooth for perforations 210. The designated exit faces of the perforated plates 209 and 210 are left in a roughened state. These variations in smoothness are designed to facilitate dispersion.

The plate 201 contains two openings on either side of the slot. Example geometries for the openings are circular holes 44.5 mm in diameter (holding filters 211) and 50.8 mm in diameter (holding membrane 212). The difference in diameter in the example is useful for correctly placing membranes (all of which may have a similar appearance) in the holes. In the upper hole a superoleophobic, hygroscopic membrane 211 allows the selective passage only of extraction fluid, while in the lower hole a hydrophobic, oleophilic membrane allows the selective passage only of fuel. Example dimensions of the filters are 47.5 mm in diameter for filter 211 and 53.8 mm in diameter for filter 212. The filters are centered in the holes such that a uniform overlap of 3 mm exists with the plate 201. The membranes 211 and 212 are secured to the plate 201 by means of adhesive elements 213 and 214. An example of an adhesive is the adduct of the diglycidyl ether of bisphenol A (DGEBA) and 4,4-oxydianiline (ODA). An alternate example of an adhesive system is a set of six pairs of neodymium magnets, each magnet having the form of a disc 6.35 mm in diameter and 3.17 mm in height, placed so that magnets of opposite polarity are paired on either side of the filter where it overlaps the plate.

During operation of embodiments of the invention, the separator plate assembly 8 functions as follows in examples where the extraction fluid exhibits a higher density than the fuel and tends to sink due to the influence of external forces such as gravity. A mixture of fuel and extraction fluid entering the upper section is selectively filtered such that extraction fluid passes selectively downward through filter 211 while fuel is retained. The downward flow of extraction fluid creates local pressure which forces the extraction fluid through the perforations 210, where it mixes with fuel flowing upward. Concurrently, fuel entering the bottom portion of the assembly is selectively passed through the filter 212. The upward flow of fuel creates local pressure which forces the fuel through the perforations 209, where it mixes with extraction fluid flowing downward. Each mixing section is formed by either the union of two stacked assemblies, or by the union of one assembly and the filter 7, or by the union of one assembly and the filter 10. Each mixing section formed by the union of two assemblies rotated 180° horizontally with respect to each other contains four walls, two perforated inlets walls for the introduction of fuel and extraction fluid, respectively, one wall containing a superoleophobic, hygroscopic filter that serves as an outlet for extraction fluid only, and one wall containing a hydrophobic, oleophilic filter that serves as an outlet for fuel only. Additional sections formed by the assemblies enclosed within the tube 2 provide a connecting fluid path between the outlet filters and the perforated inlets for the mixing chambers.

In other embodiments of the invention, the filter 7 and/or any filters contained within the separators 8 may be oleophobic rather than superoleophobic. In embodiments, the filters 7, 10 and/or any filters contained within the separators 8 may be described as amphiphobic or superamphiphobic. The overarching principle for selection of these filters, as understood by those skilled in the art, is to provide filters that selectively allow the passage of only the fuel phase and filters that selectively allow the passage of only the extraction fluid. The labels "superoleophobic," "oleophobic," "hydrophobic," "hydrophilic," and "oleophilic" herein serve as a convenience for the sake of describing the invention, and are not intended to strictly limit the selection of materials for the filters.

The following examples illustrate particular properties and advantages of some of the embodiments of the present disclosure. Furthermore, these are examples of reduction to practice of the present disclosure and confirmation that the principles described in the present disclosure are therefore valid but should not be construed as in any way limiting the scope of the invention.

EXAMPLE 1

Superoleophobic, hygroscopic membrane filters were prepared by dip coating 25 mm diameter circles of 200×200 mesh 304 stainless steel sheeting (#9656T191, McMaster-Carr) in a 50 mg/mL (total solutes) solution of poly(ethylene glycol) diacrylate ("PEGDA") (average Mn 700), 2-hydroxy-2-methyl propiophenone crosslinker (PEGDA:crosslinker ratio was 95:5 wt:wt), and fluorodecyl POSS (20 wt. % of total solutes) in Asahiklin AK225G. The dip coated mesh was then dried and cured under 254 nm ultraviolet light, in air, using a UVP CX-2000 (UVP, LLC) crosslinking oven at a total dose of 1 J/cm$^2$ per side.

EXAMPLE 2

Figure 2:
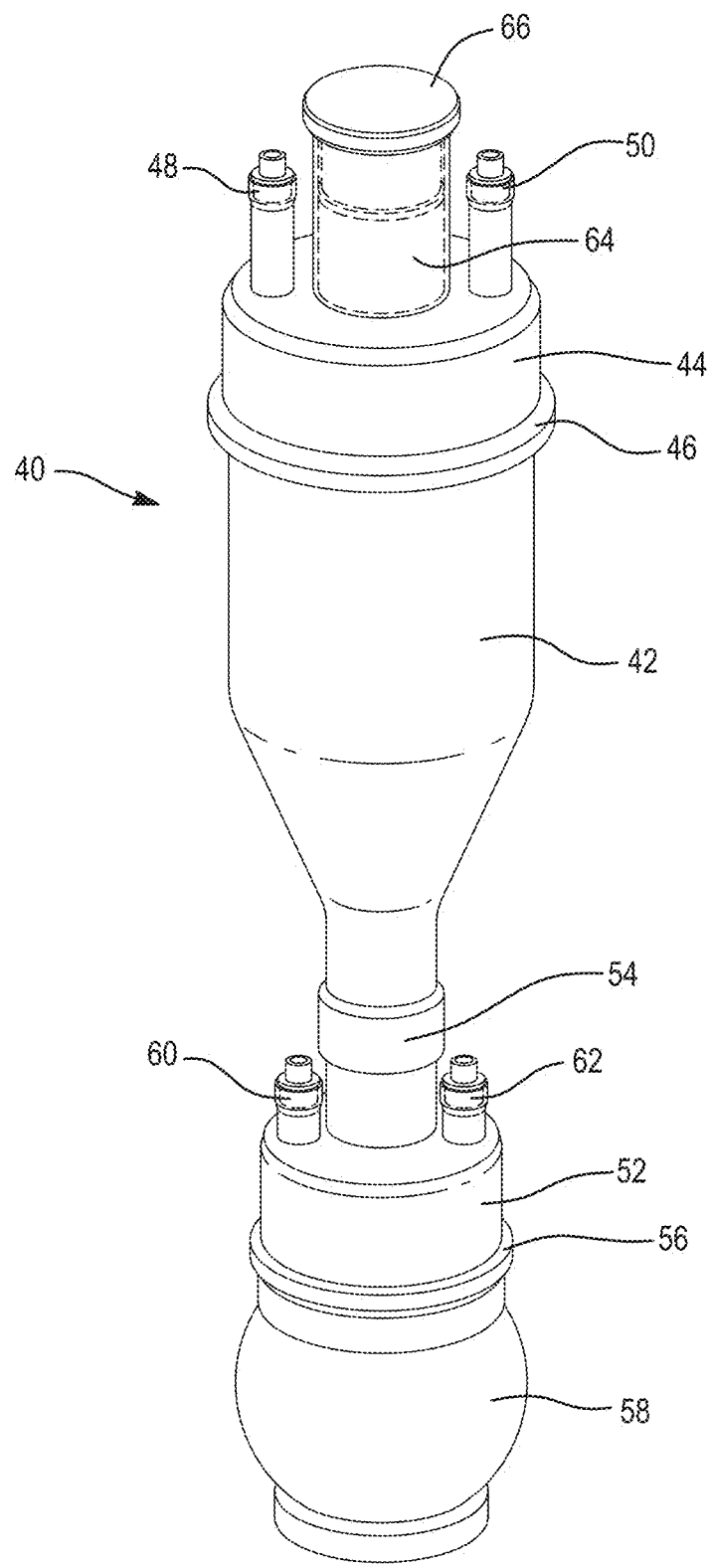
FIG. 2 is a photograph of an exemplary extraction apparatus before installation of inlet and outlet tubing and internal separation filters, constructed in accordance with one embodiment of the present disclosure.

A fuel treatment apparatus 40, as shown in FIG. 2, was constructed, wherein a glass chromatography column 42 (#5862-58, Ace Glass Inc., with #50 threaded bottom and 150 mm flange top) was fitted with a 150 mm diameter column head 44 (first column head) (#5860-32, Ace Glass, Inc. with one central #50 threaded port and two #15 threaded side ports 48, 50) at the top via the 6 inch flange 46. A second column head 52 (#5860-32, Ace Glass, Inc.) was connected to the bottom of the column via the #50 threaded port 54 using a polytetrafluoroethylene ("PTFE") adapter (#5841-52, Ace Glass, Inc.). The 6 inch flange 56 of the bottom column head 52 was connected to a 5000 mL round bottomed flask 58 (#6533-07, Ace Glass Inc.). The total volume of the apparatus, including the round bottom flask 58 and column head spaces 44, 52 was approximately 17 L. The #15 threaded side ports 60, 62 on the bottom head 52 were used as the fuel inlet port and extraction fluid outlet port. The two #15 threaded ports 48, 50 on the upper column head 44 were fitted so as to be used as the extraction fluid inlet port and fuel outlet port. The large port 64 on the upper first column head 44 was capped with a threaded PTFE stopper 66.

Although not readily shown in FIG. 2, for each inlet port, fluorinated ethylene copolymer ("FEP") ⅛ inch inner diameter and ¼ inch outer diameter tubing (#52355K32, McMaster-Carr) was passed through a 15 mm PTFE bushing (#7506-27, Ace Glass) and fitted to a brass spray nozzle (0.04 inch hole, full cone, #3178K77, McMaster-Carr). Each bushing was secured to the appropriate #15 threaded port 48, 50, 60, 62, and the tubing end was held in place by either by passing it through a hole in a filter holder (not shown), or, for the extraction fluid inlet, allowing it to hang vertically in the center of the apparatus 40. For each outlet port, additional sections of FEP tubing (#52355K32, McMaster-Carr) were passed through 15 mm PTFE bushings (#7506-27, Ace Glass, Inc.), which were secured to the appropriate #15 threaded port 60, 62. The inlet and outlet tubing were then fitted to storage vessels for the appropriate fluid. Two peristaltic pumps were used to control the inlet flow rates. Flow rates through exit ports were not controlled with external pumps.

A superoleophobic, hygroscopic membrane filter (formed by the method described in Example 1) was placed in the filter holder at the lower end of the main column 42 by clamping it between two sheets of Silpak (RZ2364, 10 parts "A" to 1 part "B", cured overnight at room temperature) silicone, which were custom molded to precisely fit the contours of the column 42. Before clamping, a polyurethane sealant (Marine 920FS, Bostik, Inc.) was applied at the outer edges of the mesh circle to hold the filter in place. Aligned 0.25 in holes were punched in both silicone sheets, and the FEP tubing (fuel inlet line) was passed through these holes in order to secure the inlet line in place.

EXAMPLE 3

Figure 3:
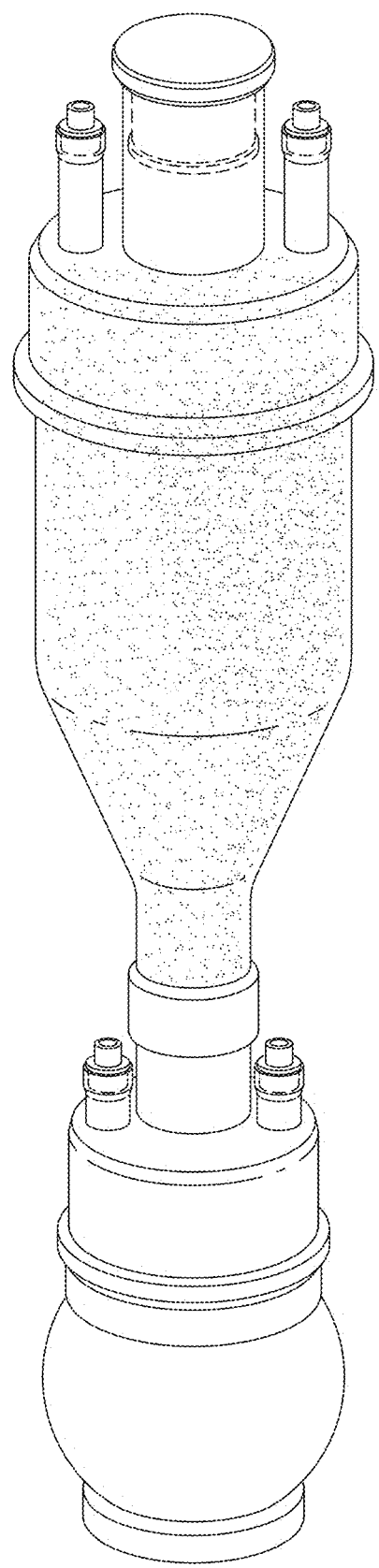
FIG. 3 is a photograph of an exemplary extraction apparatus during operation according to one embodiment of the present disclosure.

The fuel utilized for extraction was standard grade RP-1 obtained from the Air Force Research Laboratory, Aerospace Systems Directorate. The extraction fluid was a 10:1 by volume ratio of isopropanol (99%, Nexeo Solutions) and de-ionized water The assembled extraction apparatus 40 described in Example 2 was filled with IPA:water (10:1 v:v) to a level just above the extraction fluid inlet line nozzle (approximately 80% full) through the extraction fluid exit port with a peristaltic pump at 1000 mL/min. The large #50 stopper 66 at the top column head 44 was removed and RP-1 was introduced into the column 42 via the fuel inlet line at 60 mL/min and IPA/water was simultaneously introduced via the extraction fluid inlet line at 60 mL/min. A liquid-liquid emulsion then formed in the column 42. After approximately 10 min, the total liquid level had reached the fuel exit port. IPA/water was then allowed to flow out of the extraction fluid exit port until the total liquid level had dropped just below the flange 46 of the upper head 44. The IPA/water inlet pump was then shut off for approximately 5 min while the fuel feed was continued at 60 mL/min. This step was performed to induce formation of an RP-1 phase at top of the column. At this point, flow through the extraction fluid exit port was stopped and IPA/water injection was resumed at 60 mL/min. When the total liquid level had once again reached the fuel exit port, the #50 thread was capped (stopper 66) and RP-1 was allowed to exit through the fuel exit port. The extraction fluid injection was then adjusted to 40 mL/min. The extraction fluid injection rate, fuel exit flow rate and extraction fluid exit flow rate were then repeatedly adjusted, as needed, throughout the extraction operation to control the distance of the interface from the fuel exit port and the total liquid level During operation, the liquid mixture above the superoleophobic, hygroscopic membrane filter (i.e., within the column 42 and the top column head 44) remained cloudy, while below the filter (i.e., within the bottom column head 52 and the round bottom flask 58) the fluid remained clear. These observations support a conclusion that the superoleophobic, hygroscopic membrane filter functioned correctly by rejecting the passage of fuel while permitting the passage of extraction fluid. Standard grade RP-1 contains a trace amount of red dye for tax accounting purposes. During the run, the extraction fluid attained a pink color, starting with the emulsified region above the superoleophobic, hygroscopic membrane filter and spreading over about 2.5 hr to the extraction fluid exit port. The presence of the dye confirmed that trace contaminants were successfully transferred from the RP-1 to the extraction fluid. FIG. 3 is a photograph acquired during operation of the extraction apparatus operation. A total of 5 gallons of RP-1 was injected into the apparatus 40 during the run. At the completion of the run, both peristaltic pumps were stopped and the RP-1 layer remaining in the column 42 was carefully removed with a glass pipette and injected into the RP-1 collection container connected to the fuel exit port. The liquid that remained in the column 42 was pumped out through the extraction fluid outlet port into an IPA/water collection container. The amount of RP-1 collected after extraction was approximately 90% of the volume of the starting material.

EXAMPLE 4

A sulfur speciation analysis (ASTM D-5623) was performed by Intertek, Inc. on the as-received standard grade RP-1 and the RP-1 collected from the fuel exit port during the operation of the fuel extraction apparatus as described above in Example 3. Tables 1 and 2, below, summarize the results for pre-treatment and post-treatment RP-1, respectively.

TABLE 1

| Pre-treatment RP-1 | |
|---|---|
| Sulfur Compounds by GC-SCD (Sulfur Speciation) | Concentration (ppm) |
| C2 Thiophenes | <0.1 |
| C3-C4 Thiophenes | 1.6 |
| C5 Thiophenes | 6.3 |
| C6 Thiophenes | 6.1 |
| C7 Thiophenes | 5.8 |
| C8-C9 Thiophenes | 4.9 |
| C10 Thiophenes | 1.3 |
| C11 Thiophenes | 0.9 |
| C12+ Thiophenes | 2.0 |

TABLE 2

| Post-treatment RP1 | |
|---|---|
| Sulfur Compounds by GC-SCD (Sulfur Speciation) | Concentration (ppm) |
| C2 Thiophenes | 0.3 |
| C3-C4 Thiophenes | 1.4 |
| C5 Thiophenes | 3.7 |
| C6 Thiophenes | 3.5 |
| C7 Thiophenes | 4.1 |
| C8-C9 Thiophenes | 2.9 |
| C10 Thiophenes | 0.6 |
| C11 Thiophenes | 0.6 |
| C12+ Thiophenes | <0.1 |

EXAMPLE 5

In this example, batch separation of an oil-soluble red dye, Disperse Red 1, from dodecane using dimethyl formamide (DMF) as an extractant and sodium dodecyl sulfate (SDS) as the surfactant is described. The superoleophobic, hygroscopic smart membrane filter in this example, and according to certain variations of the present teachings, is formed as follows: Cellulose-based filter papers (commercially-available from Whatman) and wipes (commercially-available from Contec) are treated using oxygen plasma for 5 minutes and subsequently exposed to vapor phase of heptadecafluoro-1,1,2,2-tetrahydrodecyl triethoxysilane (commercially-available from Gelest) for 20 hours at ambient conditions (e.g., ambient pressure and room temperature).

A second conventional hydrophobic, oleophilic membrane filter is fabricates as follows: Cellulose-based filter papers (pore size of about 25 μm) are dip-coated with 2.5 mg/mL solutions of n-octadecyltrichlorosilane (commercially-available from Gelest) in toluene for 30 minutes at ambient conditions. Dip-coated filter papers are then baked at 70° C. in an oven for 2 hours and thoroughly rinsed with ethanol. These filter papers allow dodecane and methyl oleate to permeate through while preventing permeation of DMF and water. Another conventional membrane that allows the permeation of heptane, but repels the ethanol-enriched aqueous phase and methanol-enriched aqueous phase, is fabricated by dip-coating of cellulose-based filter papers (pore size about 25 μm) in 10 mg/mL solutions of poly(methylmethacrylate) in Asahiklin AK-225 (commercially-available from Structure Probe, Inc) for 30 minutes at room temperature/ambient conditions. Subsequently, the filter papers are dried at room temperature with nitrogen gas for 5 minutes.

All measurements of contact angle are conducted using a Ramé-Hart 200-F1 goniometer. All contact angles reported here are measured by advancing or receding a small volume of liquid (about 2 μl) onto the surface using a 2 ml micrometer syringe (Gilmont). At least three measurements are performed on each substrate. The typical error in measurements is ±2°. The surface morphology of the membranes used in this work was characterized using a Hitachi SU8000 scanning electron microscope at 10 kV.

FIGS. 4A-4B show droplets of ethanol (dyed blue), DMF (dyed green), hexadecane (dyed red) and dodecane (dyed yellow) on a superoleophobic, hygroscopic membrane filter fabricated using the filter paper (pore size=2.5 μm) and the wipe as discussed above, respectively. Insets show the morphologies of the respective filter paper and wipe surfaces. The hexadecane in FIG. 4A has a measured contact angle of 104° and the dodecance of 95°. In FIG. 4B, hexadecane has a measured contact angle of 138° and the dodecance of 115°. FIG. 4C shows time of wetting for a series of alcohols on the smart membrane shown in FIG. 4A. The times are t=0 seconds, t=5 seconds, t=14 seconds, and t=28 seconds. Insets show sequential wetting of four alcohol droplets in the order of decreasing Hansen hydrogen bonding parameter.

EXAMPLE 6

A batch separation apparatus 70 is shown in FIG. 6A, which includes two vertical glass tubes 72, 74 with the superoleophobic, hygroscopic membrane filter (pore size=2.5 μm) as formed above in Example 5, sandwiched therebetween. First, dodecane containing the dye is emulsified with DMF using SDS as the surfactant. The dodecane droplet number size distribution indicates that the greatest fraction is in the range of 1-20 μm. A 50:50 dodecane:DMF volume ratio is used. Within a few minutes of adding this emulsified mixture to the upper glass tube 72, the superoleophobic, hygroscopic membrane filter allows the dye-enriched DMF (polar raffinate phase) to permeate through solely under gravity, while preventing the permeation of the emulsified droplets of dye-depleted dodecane (non-polar extract phase; see FIG. 6B). After separation, the dye-depleted dodecane retained above the membrane is almost perfectly transparent, indicating efficient extraction.

In the batch separation operation described in this example, the retentate or raffinate will continue to accumulate above the membrane, eventually breakthrough and permeate through the membrane.

EXAMPLE 7

In order to overcome the shortcomings of batch separation, a continuous separation methodology is provided in this example that combines surfactant-enhanced extraction and superoleophobic, hygroscopic smart membrane-based separation into a single unit operation. A single unit continuous separation apparatus 100 (see FIGS. 5 and 6C) has a contact vessel or contacting chamber 104 where the feed phase and the extractant phase with dissolved surfactant are continuously fed using syringe pumps 101. A gravity-driven countercurrent flow design is used here with the lower density liquid fed from the bottom of the chamber 104 and the higher density liquid fed from the top of the chamber 104. The feed phase and the extractant phase are emulsified in-situ in the chamber using a mechanical stirrer 114.

With reference to FIG. 5, a first feed stream 102 is thus introduced into the mixing chamber or contact vessel 104. The feed stream 102 has at least one component or impurity to be separated therefrom and may be a non-polar liquid. The contact vessel 104 is also equipped with two membranes operating in parallel—a smart superoleophobic, hygroscopic membrane 110 in accordance with certain variations of the present teachings and a conventional hydrophobic and oleophilic membrane 112. The contact vessel 104 also has a stirring mechanism or impeller 114. An extractant 120 is also introduced into the contact vessel 104, which may be a polar liquid and have a relatively higher density than the feed stream 102. The extractant 120 may also be premixed with and contain a surfactant. Thus, the feed stream 102 and extractant 120 (with a surfactant) may be mixed together within the contact vessel 104 to form an emulsion 122.

While the superoleophobic, hygroscopic membrane smart filter membrane 110 allows a polar liquid (extract stream 130, which may contain the extractant 120, surfactant, and at least one component to be removed from the feed stream 102) to pass through and prevents the permeation of a non-polar liquid (raffinate stream 132, which may contain a remainder of components of the feed stream 102 excluding the component to be removed), the second conventional membrane 112 allows a lower surface tension liquid (raffinate stream 132) to pass through and prevents the permeation of a higher surface tension liquid (extract 130). Note that the membrane separation occurs continuously and simultaneously along with emulsification and extraction. Further, the emulsion is broken as extract stream 130 and raffinate stream 132 pass through the superoleophobic, hygroscopic membrane smart filter membrane 110.

A photograph shown in FIG. 6C of such a continuous separation apparatus is used for continuous surfactant-enhanced extraction and smart membrane-based separation of dodecane-in-DMF emulsion. The superoleophobic, hygroscopic membrane filter 110 used is formed as described in Example 5. A conventional second membrane filter 112 formed as described in Example 5 is also incorporated into a side wall of the contacting vessel or chamber. The dodecane containing the dye is emulsified with DMF using SDS as the surfactant is the same as discussed above in Example 5.

Using this continuous separation methodology, a dye (Disperse Red 1) is extracted from dodecane. Dodecane containing 30 ppm of the dye and DMF with dissolved SDS are fed to the mixing or contact chamber 104 with 90:10 dodecane:DMF volumetric flow rate ratio. Here, SDS is chosen as the surfactant because it is immiscible with dodecane (the desired phase). The polar dye-enriched DMF phase continuously permeates through the superoleophobic, hygroscopic membrane filter 110, while the dye-depleted dodecane phase with lower surface tension continuously permeates through the conventional membrane 112 on the side-wall.

The dye-enriched DMF phase (extract) continuously passes through the smart membrane 110 at the bottom, while the dye-depleted dodecane phase (raffinate) passes through the conventional membrane 112 on the side-wall. FIG. 6D shows UV-Vis absorbance data for the dye-depleted dodecane phase obtained with and without surfactant-enhanced extraction. Also included is the data for calibration samples. The UV-Vis absorbance measurements indicate that the dye-depleted dodecane phase contains ≤0.5 ppm of dye. Further, it is also evident from the UV-Vis measurements that the purity of the permeate after surfactant-enhanced extraction increases 400% compared to that from a separation without the surfactant (see FIG. 6D).

Density measurements and refractive index measurements indicate that the DMF-rich phase contains approximately 3.5 wt. % of dodecane and dodecane-rich phase contains about 4.0 wt. % of DMF. These values are comparable to the miscibility of dodecane in DMF and DMF in dodecane at room temperature. Experimentally-measured fluxes of the extract and the raffinate phases through the membranes are measured to be 35 $Lm^{-2}h^{-1}$ and 480 $Lm^{-2}h^{-1}$, respectively. This is believed to be the first-ever demonstration of an extremely energy-efficient, continuous, single unit operation that combines surfactant-enhanced extraction and smart membrane-based solely-gravity driven separation to separate miscible components down to a purity of a few parts per million.

When feasible, it is economically desirable to use less expensive extractants for extraction. In order to address this, the percent solute extracted from the feed using various ratios of feed:extractant volumetric flow rates in the continuous separation apparatus are measured. FIG. 6E shows the percentage of dye removal from dodecane using different dodecane:DMF volumetric flow rate ratios. The feed to extractant volumetric ratios are as follows: Feed:Extractant (vol:vol), 97:3, 95:5, 92:8, and 90:10. The inset shows the dodecane-rich phase after separation. In extracting Disperse Red 1 from dodecane using DMF, even a 95:5 feed:extractant volumetric flow rate resulted in >80% dye removal (see FIG. 6E).

The simplicity and versatility of such a continuous separation methodology permits separation of a wide variety of commercially relevant miscible components.

EXAMPLE 8

This example separates methanol from biodiesel. Biodiesel is produced through a process known as transesterification where vegetable oils or animal fats are chemically reacted with alcohols such as methanol. The reaction produces a new chemical compound called methyl ester and byproducts such as glycerol and excess methanol. After the reaction, however, methyl ester must be purified from glycerol and other byproducts. Although glycerol is easily separated from biodiesel through centrifugation or decantation, because of its poor solubility and significant density difference, the separation of methanol requires energy-intensive methodologies like vacuum distillation.

In this example, separation of methanol from methyl oleate using water as an extractant and SDS as the surfactant for emulsification is demonstrated. Here methyl oleate is used as a representative biodiesel. Methyl oleate containing 10 vol. % of methanol and water with dissolved SDS are fed to the separation chamber 104 (contacting vessel or chamber) in a gravity-driven countercurrent flow as discussed above in Example 7 and shown in FIGS. 5 and 6C. After emulsification, the methanol-enriched aqueous phase continuously permeates through the superoleophobic, hygroscopic membrane filter 110 (formed as described in Example 5) at the bottom, while the methanol-depleted methyl oleate phase continuously permeates through the conventional membrane 112 on the side-wall (also formed as described in Example 5).

FIG. 7A shows the percent methanol removal from methyl oleate data obtained with and without surfactant-enhanced extraction using different methyl oleate:water volumetric flow rate ratios. The feed to extractant volumetric ratios are as follows: Feed:Extractant (vol:vol), 90:10, 70:30, and 50:50. As can be seen, the emulsification step preceding separation enhances overall percentage of methanol removed from the methyl oleate.

Refractive index measurements indicate that 95% of methanol can be removed from methyl oleate using a 50:50 feed:extractant volumetric flow (see FIG. 7A). As might be expected, surfactant-enhanced extraction facilitates more efficient removal of methanol compared to a separation without the surfactant, as shown in FIG. 7A.

EXAMPLE 9

In this example, separation of azeotropes in accordance with certain aspects of the present disclosure is shown. Extraction is a useful alternative for the separation of azeotropes (i.e., constant boiling mixtures), which cannot be separated by simple distillation. The separation of oil-alcohol mixtures, including azeotropes, is highly desirable in biodiesel production, refining vegetable oils and petrochemical industries, among others. In this example, heptane is used as a representative oil, ethanol as a representative alcohol and the separation of heptane-ethanol azeotrope is demonstrated by using water as an extractant and SDS as the surfactant for emulsification. SDS is chosen as the surfactant because it is immiscible with heptane (the desired phase). Initially, the heptane-ethanol azeotrope and water, with dissolved SDS, are fed into the separation chamber of a continuous separation apparatus 100 like in Example 7 and shown in FIGS. 5 and 6C.

After emulsification, the ethanol-enriched aqueous phase continuously permeates through the superoleophobic, hygroscopic membrane filter 110, while the ethanol-depleted heptane phase continuously permeates through the conventional membrane 112 on the side-wall.

Thus, ethanol is removed from an ethanol-heptane azeotrope, with percent ethanol removed shown in FIG. 7B. Different azeotrope:water (extractant) volumetric flow rate ratios are used. The feed to extractant volumetric ratios are as follows: Feed:Extractant (vol:vol), 97:3, 95:5, 92:8, 90:10, and 50:50.

Refractive index measurements indicate that about 99% ethanol can be extracted from the azeotrope using a 50:50 azeotrope:extractant volumetric flow rate (see FIG. 7B).

EXAMPLE 10

Separation of sulfur compounds from oils in accordance with certain aspects of the present teachings are set forth in this example. With tighter environmental regulations and government mandates, there is a significant push towards removing sulfur compounds from oils. In this example, dodecane is used as a representative oil and the removal of sulfur compounds t-butyl thiol and benzothiophene from dodecane is demonstrated here by using DMF as an extractant and SDS as the surfactant for emulsification. Here, SDS is chosen as the surfactant because it is immiscible with dodecane (the desired phase). Dodecane containing 50 ppm t-butyl thiol (or 30 ppm benzothiophene) and DMF with dissolved SDS are fed to the continuous separation chamber 100 (FIG. 5) in a gravity-driven countercurrent flow, as discussed above in Example 7 and shown in FIG. 7C.

After emulsification, the sulfur compound-enriched DMF phase continuously permeates through the superoleophobic, hygroscopic membrane filter 110 (FIG. 5) as formed in Example 5, while the sulfur compound-depleted dodecane phase continuously permeates through the conventional membrane 112 (FIG. 5) on the side-wall (also formed as described in Example 5). UV-Vis absorbance measurements indicate that about 80% of benzothiophene can be removed from dodecane using a 50:50 feed:extractant volumetric flow rate (see FIG. 7C). Also GCMS (Gas Chromatography Mass Spectroscopy) measurements show that about 60% of t-butyl thiol is extracted using a 50:50 feed:extractant volumetric flow rate (see FIG. 7C). As might be expected, higher extraction efficiencies are achieved with higher feed:extractant volumetric flow rates.

FIG. 7C shows the percent sulfur compound (for both benzothiophene and t-butyl thio) removal from dodecane using different dodecane:DMF volumetric flow rate ratios. The feed to extractant volumetric ratios are as follows: Feed:Extractant (vol:vol), 90:10, 70:30, and 50:50. Insets show the wetting behavior of the polar liquid and the non-polar in each separation on a smart membrane fabricated using a filter paper (pore size=2.5 μm).

The present disclosure provides a new extremely energy-efficient, liquid-liquid extraction process and devices for conducting such processes. The devices may be a continuous single unit operation that combines (a) extraction using surfactant-stabilized emulsions, and (b) solely-gravity driven (i.e., without any external energy) separation of these emulsions using smart membranes, to separate miscible components down to a purity of a few ppm. Such methods are applicable to a wide range of separations. Further, such separations can be directly incorporated into many mainstream commercial separation operations.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A method of liquid-liquid extraction comprising:
   creating an emulsion by combining a feed stream, an extractant, and a surfactant, wherein the feed stream comprises a first component that is a contaminant or impurity present at an initial amount and the feed stream is selected from a group consisting of: a non-polar feed stream and an azeotrope comprising the non-polar feed stream;
   removing a portion of the first component from the emulsion by contacting the emulsion with a first side of a superoleophobic and hygroscopic membrane filter to facilitate passage of the first component and the extractant through the superoleophobic and hygroscopic membrane filter to a second side of the superoleophobic and hygroscopic membrane filter; and
   collecting a purified product having the portion of the first component removed.

2. The method of claim 1, wherein the removing the portion of the first component by contacting includes gravity-feeding the emulsion to the first side of the superoleophobic and hygroscopic membrane filter at ambient conditions.

3. The method of claim 1, wherein the feed stream selected from a group consisting of: the non-polar feed stream and the azeotrope comprising the non-polar feed stream comprises a plurality of distinct components including the first component and a second component, wherein the first component and the second component are miscible with one another.

4. The method of claim 1, wherein the feed stream selected from a group consisting of: the non-polar feed stream and the azeotrope comprising the non-polar feed stream comprises a plurality of distinct components including the first component and a second component, wherein the first component comprises a polar molecule and the second component comprises a non-polar molecule.

5. The method of claim 1, wherein the feed stream comprises a plurality of distinct components and is a fuel feedstock, wherein the first component is a contaminant and a remainder of the plurality of distinct components are fuel components, so that the removing of the portion of the first component by contacting the emulsion with the superoleophobic and hygroscopic membrane filter separates the first component from the fuel components so that the purified product is a refined fuel.

6. The method of claim 1, wherein the portion of the first component removed from the purified product is about 99.99 weight % of the initial amount of the first component in the feed stream.

7. The method of claim 1, wherein the removing is continuously conducted in a single unit operation of a separator device, wherein the emulsion is gravity fed from the first side to the second side of the superoleophobic and hygroscopic membrane filter to continuously separate the first component and the extractant from the emulsion.

8. The method of claim 7, wherein the separator device further comprises: a second membrane filter that is oleophilic and hydrophobic in fluid contact with the emulsion that continuously removes a remainder of the feed stream from the emulsion.

9. The method of claim 8, wherein the second membrane filter is positioned above the superoleophobic and hygroscopic membrane filter with respect to a direction the emulsion is gravity fed from the first side to the second side of the superoleophobic and hygroscopic membrane filter.

10. The method of claim 7, further comprising: filtering a selectively extracted extraction fluid through a selective stationary absorbent.

11. The method of claim 1, wherein the first component that is a contaminant or impurity in the feed stream comprises one or more of a sulfur-containing compound, a nitrogen-containing compound, or an aromatic compound.

* * * * *